Figure 1:
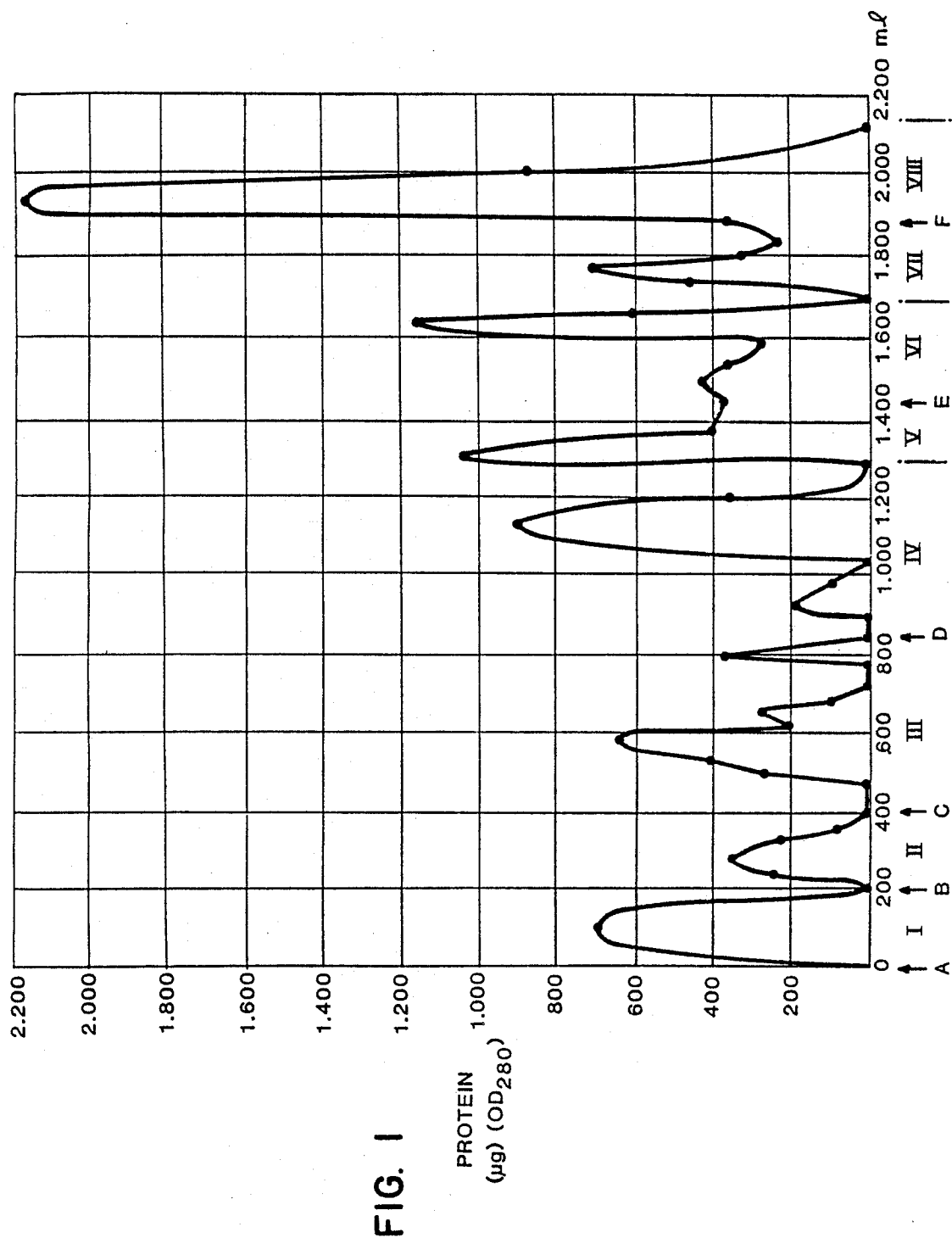

United States Patent [19]

Bogoch

[11] Patent Number: 4,840,915
[45] Date of Patent: * Jun. 20, 1989

[54] METHOD FOR DIAGNOSING MALIGNANT TUMORS

[75] Inventor: Samuel Bogoch, St. George, Bermuda

[73] Assignee: Brain Research, Inc., New York, N.Y.

[ * ] Notice: The portion of the term of this patent subsequent to Apr. 1, 1997 has been disclaimed.

[21] Appl. No.: 538,492

[22] Filed: Oct. 3, 1983

Related U.S. Application Data

[60] Continuation-in-part of Ser. No. 281,883, Jul. 9, 1981, and a continuation-in-part of Ser. No. 271,645, Jul. 8, 1981, Pat. No. 4,486,538, each is a continuation-in-part of Ser. No. 922,799, Jul. 7, 1978, Pat. No. 4,298,590, which is a continuation of Ser. No. 19,078, Mar. 9, 1978, abandoned, which is a continuation-in-part of Ser. No. 941,940, Sep. 13, 1980, abandoned, which is a division of Ser. No. 852,200, Nov. 17, 1977, Pat. No. 4,196,186, which is a continuation of Ser. No. 621,112, Oct. 9, 1975, abandoned, which is a continuation-in-part of Ser. No. 553,075, Feb. 25, 1975, abandoned, and a continuation-in-part of Ser. No. 550,432, Feb. 18, 1975, abandoned, and a continuation-in-part of Ser. No. 450,404, Mar. 12, 1974, abandoned, and a continuation-in-part of Ser. No. 385,451, Aug. 3, 1973, abandoned, and a continuation-in-part of Ser. No. 286,172, Jul. 23, 1981, which is a continuation of Ser. No. 101,127, Dec. 7, 1979, abandoned, which is a continuation of Ser. No. 852,200, Nov. 17, 1977, Pat. No. 4,196,186.

[51] Int. Cl.$^4$ .................. G01N 33/544; G01N 33/531
[52] U.S. Cl. ..................................... 436/530; 436/543; 436/805; 436/811; 436/813; 436/824
[58] Field of Search ............... 436/530, 543, 805, 811, 436/813, 824

[56] References Cited

U.S. PATENT DOCUMENTS 4,196,186 4/1980 Bogoch .......................... 436/503 X Primary Examiner—Christine M. Nucker
Attorney, Agent, or Firm—Kenyon & Kenyon

[57] ABSTRACT

This invention is directed to a novel group of compounds, herein termed Recognins. Recognins are made by treating malignant tumor cells or artificial cancer cells and separating the desired products. The Recognins may be used to prepare their Chemoreciprocals, i.e., by contacting the Recognins or the Recognins on a support with body fluids. These Chemoreciprocals are useful for diagnostic and therapeutic purposes, i.e., for diagnosing and treating cancers. The Chemoreciprocals are substances which react with immunochemical-like specificity with a Recognin in vivo or in vitro, e.g., in a quantitative precipitin test, in Ouchterlony double diffusion or in immunofluorescence.

8 Claims, 2 Drawing Sheets

PLATE A  LOADED 4-21-78 {10 AM / 11 PM}
FIG. 2  PHOTO 4-23-78 7 AM
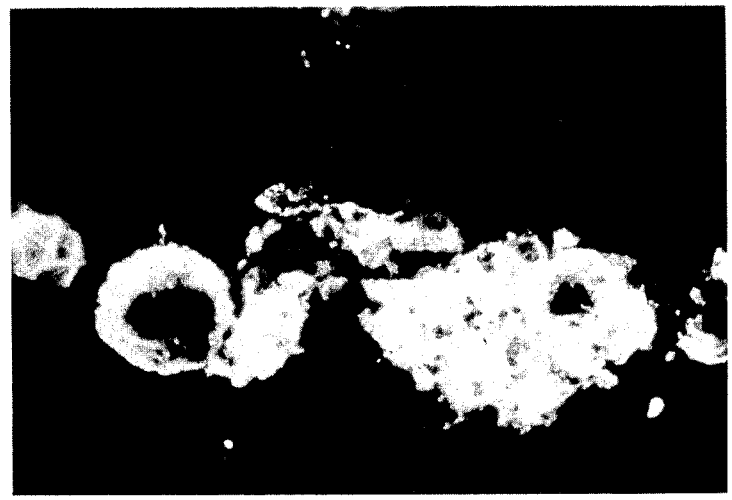
FIG. 3a
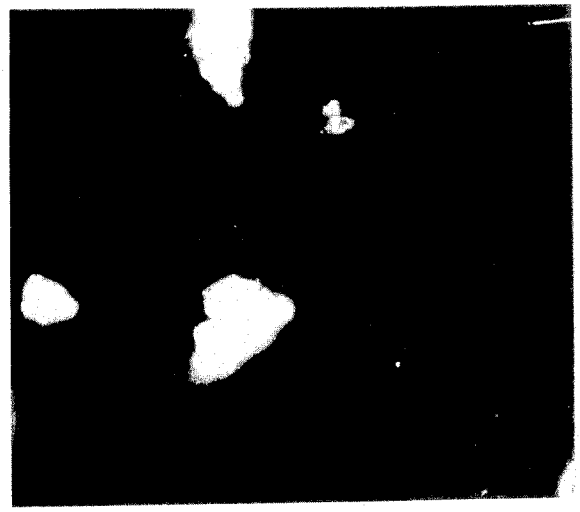
FIG. 3b

METHOD FOR DIAGNOSING MALIGNANT TUMORS

CROSS REFERENCES TO RELATED APPLICATIONS

This application is a continuation-in-part of application Ser. No. 281,883, filed July 9, 1981 and application Ser. No. 271,645, filed June 8, 1981, now U.S. Pat. No. 4,486,538; which in turn are continuations-in-part of application Ser. No. 922,799, filed July 7, 1978, now U.S. Pat. No. 4,298, 590 and also a continuation of application Ser. No. 19,078, filed Mar. 9, 1978, now abandoned; which in turn is a continuation-in-part of application Ser. No. 941,940, filed Sept. 13, 1980, now abandoned; which in turn is a divisional of application Ser. No. 852,200, filed Nov. 17, 1977, now U.S. Pat. No. 4,196,186; which in turn is a continuation of application Ser. No. 621,112, filed Oct. 9, 1975, now abandoned; which in turn is a continuation-in-part of each of applications Ser. No. 553,075, filed Feb. 25, 1975, now abandoned; Ser. No. 550,432, filed Feb. 18, 1975, now abandoned; Ser. No. 450,404, filed Mar. 12, 1974, now abandoned; and Ser. No. 385,451, filed Aug. 3, 1973, now abandoned; and this application is also a continuation-in-part of application Ser. No. 286,172, filed July 23, 1981; which in turn is a continuation of application Ser. No. 101,127, filed Dec. 7, 1979, now abandoned; which in turn is a continuation of application Ser. No. 852,200.

This invention is directed to a novel group of compounds, herein termed Recognins. Recognins are made by treating malignant tumor cells or artificial cancer cells and separating the desired products. The Recognins may be used to prepare their Chemoreciprocals, i.e., by contacting the Recognins or the Recognins on a support with body fluids. These Chemoreciprocals are useful for diagnostic and therapeutic purposes, i.e., for diagnosing and treating cancers. The Chemoreciprocals are substances which react with immunochemical-like specificity with a Recognin in vivo or in vitro, e.g., in a quantitative precipitin test, in Ouchterlony double diffusion or in immunofluorescence.

One of the Recognins of the present invention is Astrocytin. Astrocytin is produced from brain tumor tissue, preferably brain glioma tumor tissue. Protein fractions containing the Astrocytin precursor are first extracted from the tissue. A preferred method of accomplishing the extraction is to treat the tissue with a neutral buffer under conditions of homogenization or other techniques to disrupt the cells and tissues in order to solubilize protein fractions which contain the Astrocytin precursor.

At this point, the Astrocytin precursor is still bound to many large molecular weight substances including protein, glyco-proteins, lipoproteins, nucleic acids, nucleoproteins, etc. The solubilized proteins are then separated from the resultant tissue extract. The extract solution from the tissue is then clarified to remove insoluble particles. The low molecular weight contaminants are then removed from the resultant solution, by a perevaporation concentration technique. The solution which is obtained is then treated to cleave Astrocytin precursor from other contaminants in order to obtain the protein fraction having a pK range between 1 and 4. Thus, for example, the solution is placed on a chromatographic column and eluted with increasingly acidic solvents. All of the fractions which are eluted in the neutral or acid range down to pK 4 are discarded and those fractions with pK range 1-4 are collected. The eluate is then treated to obtain a product having a molecular weight of about 8,000. This is accomplished, for example, by first filtering the material to remove low molecular weight substances, i.e., those below 1,000 molecular weight, and filtering again to remove those above 25,000. The fraction having a molecular weight between 1,000 and 25,000 is then further treated, i.e., by thin layer gel (TLG) chromatography, to obtain Astrocytin.

Thus Astrocytin may be produced by extracting brain glioma tumor tissue with a neutral buffer, by repeated homogenization and high speed centrifugation, separating from the resulting extract the fraction having a pK range of from about 1 to 4, separating from said fraction the substances having a high molecular weight, i.e., up to about 230,000, and isolating therefrom the product Astrocytin having a molecular weight of about 8,000.

The product Astrocytin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mu and having a molecular weight of about 8,000.

Astrocytin is also characterized by having a very high percentage of residues of glutamic acid and aspartic acid and a very high ratio of these acids to histidine. A further analysis of Astrocytin is provided below.

In a manner similar to that described above, another Recognin, called Malignin, is produced from artificial cancer cells, i.e., cancer cells grown in in vitro fermentation. Malignin has a molecular weight of about 10,000 and similar but distinct amino acid residue composition to Astrocytin, i.e., high ratios of glutamic acid and aspartic acid and high ratios of these acids to histidine. A further analysis of Malignin is provided below.

Thus, Malignin can be produced by extracting artificial brain glioma cancer cells grown in fermentation culture with a neutral buffer by repeated homogenization and high speed centrifugation, separating from the resulting extract the fraction having a pK range of about 1 to 4, separating from said fraction the substances having a high molecular weight, i.e. up to about 230,000, and isolating therefrom the product having a molecular weight of about 10,000.

The amount of Malignin produced in artificial cell fermentation and the percentage of total protein produced in artificial cell fermentation which is Malignin can be increased by growth of artificial cancer cell culture in large size growth containers.

Malignin prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mu and having a molecular weight of about 10,000.

In a manner similar to that described above, another Recognin, called Recognin M, is produced from artificial mammary cancer cells, i.e., mammary cancer cells grown in in vitro fermentation. Recognin M has a molecular weight of about 8,000 and similar but distinct amino acid residue composition to Astrocytin and Malignin i.e., high ratios of glutamic acid and aspartic acid and high ratios of these acids to histidine. The principal compositional differences between Malignin and Recognin M are that the latter has decreased amounts of aspartic acid, glutamic acid, leucine and tryosine and increased amounts of proline, glycine and alanine. A further analysis of Recognin M is provided below.

Thus, Recognin M can be produced by extracting artificial mammary cancer cells grown in fermentation culture with a neutral buffer by repeated homogenization and high speed centrifugation, separating from the resulting extract the fraction having a pK range of about 1 to 4, separating from said fraction the substances having a high molecular weight, i.e., up to about 230,000, and isolating therefrom the product having a molecular weight of about 8,000.

Recognin M prepared in accordance with this process is characterized by forming a single line precipitate with its specific anitbody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mu and having a molecular weight of about 8,000.

In a manner similar to that described above, another Recognin, called Recognin L, is produced from artificial lymphoma cancer cells, i.e., lymphoma cancer cells grown in in vitro fermentation. Recognin L has a molecular weight of about 8,000 and similar but distint amino acid residue composition to Astrocytin, Malignin and Recognin M, i.e., high ratios of glutamic acid and aspartic acid and high ratios of these acids to histidine. As compared to Malignin, Recognin L has decreased amounts of aspartic acid, glutamic acid, leucine and tryosine and decreased amonts of proline, glycine and alamine. A further analysis of Recognin L is provided below.

Thus, Recognin L can be produced by extracting artificial lymphoma cancer cells grown in fermentation culture with a neutral buffer by repeated homogenization and high speed centrifugation, separating from the resulting extract the fraction having a pK range of about 1 to 4, separating from said fraction the substances having a high molecular weight, i.e., up to about 230,000, and isolating therefrom the product having a molecular weight of about 8,000.

Recognin L prepared in accordance with this process is characterized by forming a single line precipitate with its specific antibody in quantitative precipitin tests and Ouchterlony gel diffusion tests, being soluble in water and aqueous solutions having an acid or neutral pH, and insoluble at an alkaline pH, having a spectrophotometric absorption peak wave length of 280 mu and having a molecular weight of about 8,000.

Recognins are further characterized by being capable of complexing with bromoacetylcellulose to form bromoacetylcellulose-Recognin and producing the specific antibodies Anti-Recognin upon injection into mammals, said Anti-Recognin attaching specifically to the Recognin-precursor in situ. For example, one Anti-Recognin, Anti-Malignin being toxic to brain tumor cells in vitro.

Recognins, such as Astrocytin, Malignin, Recognin M and Recognin L and similar substances are useful as products which may be introduced into a biological system to reduce foreign reactions, such as by coating a material with a Recognin. A further example may be to introduce a Recognin in order to produce the Chemoreciprocals in the biological system. They may also be used nutritionally to encourage the growth of a particular biological system of which they are a part. A further utility of Recognin is the production of Target regaents which comprise the complexes of the Recognin with a carrier to facilitate its applicability in biological systems. Thus, for example, the complex conveys the physicalchemical characteristics of the Recognin itself. The carrier should be selected from those which form a complex with the Recognin and which are substantially biologically inert.

Any substance known in the art which will form a stable complex with polypeptides or proteins may be useful for complexing with the Recognin. An example is a cellulose-based material, such as bromoacetyl-cellulose. In addition to being inert to the biological system, the carrier should be one that does not alter the specific physical-chemical properties of the Recognin which are useful for the purposes set forth herein.

The complexes of the Recognin and its carrier are useful for producing, separating and identifying its chemoreciprocal in any biological system with which it is brought into contact. The Recognin-carrier complex is also useful for stimulating the production of its chemoreciprocal precursor in any biological system into which it is introduced.

One class of Chemoreciprocals are the anti-Recognins, i.e., anti-Astrocytin, anti-Malignin, anti-Recognin M and anti-Recognin L. These may be made by injecting the Recognin into a biological system. An immunologically effective dose of Recognin is brought into contact with body tissues or fluids in a manner which induces an antibody response in accordance with techniques known in the art for producing antibodies. The anti-Recognins may be used for the delivery of materials such as diagnostic, nutritional and therapeutic agents to specific cells or sites in a biological system which comprises introducing said agent in complexed form with the anti-Recognin into the biological system. The anti-Recognins are also useful for diagnosing the presence of tumor cells in a histology section, by applying the Anti-Recognin conjugated with a labeling substance such as dyes and radioactive substances, to said section, whereby staining or radioactive labeling occurs only with tumor cells. Yet another use for anti-Recognins is for increasing the yield of other useful Chemoreciprocal products (such as TAG, described below) from a mammal which comprises injecting an immunologically effective dose of Recognin into the mammal, or other biological system.

Prior to the present invention, glycoprotein complexes were prepared from brain tissue and antibodies made to them. Separated materials known as 10B glycoproteins produced from Tay-Sachs' disease brain, were injected into rabbits and antibodies produced. These Tay-Sachs' antibodies were used in immunofluorescent studies of brain-containing tumors: only reactive normal non-tumor glia, not tumor glia, were stained by these antibodies.

In contrast, when Astrocytin was produced from tumor tissue, and antibodies to Astrocytin (Anti-Astrocytin) were produced and employed in immunofluorescent studies of brain, only tumor glia, not normal (non-tumor) glia, were stained by Anti-Astrocytin. Thus, by tissue of origin and by nature of the antibody, as well as by the specific type of cells stained, anti-Tay-Sachs' antibodies and anti-Astrocytin are clearly different products.

Another class of Chemoreciprocals is Target reagents complexed with their chemoreciprocals. For example, Astrocytin Target (the product of Astrocytin complexed with a carrier such as bromoacetylcellulose) is brought into contact with antiAstrocytin. This type of compound may be coupled with and used for the delivery of diagnostic, nutritional and therapeutic agents to specific cells or sites in a biological system. These compounds may also be used for purification procedures. For example, Anti-Astrocytin may be made by the decomplexing of Bomoacetylcellulose-Astrocytin-Anti-Astrocytin by hydrolytic treatment with an acid or proteinase enzyme. Target reagents are also useful for increasing the amount of TAG products (described below) in a biological system, such as by bringing an immunologically effective dose of Target into contact with body tissues of fluids.

Additional Chemoreciprocals are TAG reagents (Target-Attaching Globulins). The TAG products are produced by bringing Target reagents into contact with body fluids for varying periods of time to form a complex and cleaving TAG therefrom. Two useful embodiments are S-TAG and F-TAG.

A process for producing S-TAG (Slow-Target-Attaching-Globulin) comprises reacting blood serum or other body fluid with Target (e.g., Bromoacetylcelluose-Malignin, Bromoacetylcellulose-Recognin M, Bromacetylcellulose-Recognin L) for approximately two hours or more at a low temperature, e.g., about 4° C., and cleaving S-TAG from the resulting material, e.g., with dilute acid for approximately two hours at a temperature of about 37° C. The product S-TAG prepared in accordance with this process is characterized by being soluble in aqueous buffered solutions, forming a single line precipitate with its corresponding Recognin in Ouchterlony gel diffusion tests, being non-dialyzable in cellophane membranes, being retained by millipore filters which retain molecules over 25,000 molecular weight, having molecular weights in different states of aggregation as determined by thin layer gel chromatography of approximately 50,000, and multiples thereof into the macroglobulin range and having a spectrophotometer absorption peak wave length of 280 mu.

A process for producing F-TAG (Fast-Target-Attaching-Globulin) comprises reacting blood serum or other body fluid with Target (e.g., Bromoacetylcellulose-Malignin, Bromoacetylcellulose-Recognin L, Bromacetylcellulose Recognin M) for approximately 10 minutes at a low temperature, e.g. about 4° C., and cleaving F-TAG from the resulting material, e.g. with dilute acid for approximately two hours at a temperature of about 37° C. The product F-TAG prepared in accordance with this process is characterized by being soluble in aqueous buffered solutions, forming a single line precipitate with its corresponding Recognin in Ouchterlony gel diffusion tests, being nondialyzable in cellophane membranes, being retained by millipore filters which retain molecules over 25,000 molecular weight, having molecular weights in different states of aggregation as determined by thin layer gel chromatography of approximately 50,000, and multiples thereof into the macroglobulin range and having a spectrophotometer absorption peak wave length of 280 mu.

TAG products are useful for detecting cancer tumors in living mammals by determining the concentration of S-TAG and F-TAG produced by a known volume of the mammal's blood serum or other body fluid and correlating this concentration with amounts determined to be indicative of cancer. TAG products are also useful for diagnosing the presence of tumor cells in a histology section, which comprises applying TAG conjugated with a labeling substance such as dyes and radioactive substances, to said section, whereby staining or radioactive labeling occurs only with tumor cells. TAG products additionally have been found to be cytotoxic to tumor cells. TAG products are also useful for directing the delivery of diagnostic, nutritional and therapeutic agents to specific cells or sites by introducing said agents in complexed form with the TAG product.

Normal cell division in plants or animals is restricted or inhibited when the cells come to occupy fully a particular space. The mechanisms (a) by which normal cells "recognize" that they have filled the space available to them, and (b) by which the operation of this recognition mechanism in turn inhibits cell division, have both been unknown. A group of compounds have now been produced whose precursors are increased in concentration when normal recognition and learning occur, and which relate to recognition and learning in particles and cells, and with the connection of cells to each other. These compounds are termed RECOGNINS. By attempting to produce these compounds from normal cancer cells, it was discovered that they are absent as such, and that changes in their molecular structure have occurred at the same time that the cancer cells have lost their ability (a) to recognize that they have filled their normal volume, and/or (b) to stop dividing when they have filled their normal volume.

Novel compounds and methods for producing such compounds have been discovered. These new compounds are termed RECOGNINS. RECOGNINS are novel compounds which have physiochemical characteristics which mimic those configurations characteristic of cancer cells in terms of their failure to recognize and stop cell division. The use of RECOGNINS goes beyond insight into the cancer mechanism, for immediate products and methods are thereby provided which are useful in the diagnosis and treatment of cancer, and for its prevention.

Methods by which artificially cultured cells can be used to produce Recognins have been discovered. One advantage of the methods disclosed herein is that Recognins and new products from them can now be manufactured efficiently in virtually limitless quantities.

This invention transcends the field of cancer research and is immediately applicable to any and all biological systems in which it is desired to influence all growth and metabolism. Thus by the manufacture of the particular compound or compounds of appropriate cell type in artificial culture, and the further manufacture of products from these substances, specific influence may for the first time be brought to bear on any tissue, cell, cell organelle, sub-organelle molecule or molecular aggregate in any living system. Thus specific nutritional influences at critical times in development, specific diagnostic, preventative and treatment methods, and the construction of artificial bioelectrical system (as in tissue or organ transplants) can all be affected for the first time. These artificial bioelectrical systems can now be made to bear the characteristics of the specific RECOGNIN, ASTROCYTIN MALIGNIN, RECOGNIN L, RECOGNIN M, or their CHEMORECIPROCALS of the normal tissue or component which they will neighbor and thus being "recognized" as "foreign" and thus avoid the reactions to alien substances, including rejection.

Another aspect of this invention is the production of a valuable specific antibody-like product (Anti-Astrocytin) to a specific brain product (Astrocytin), permitting the use of this antibody-like product to specifically complex with and, as a specific delivery vehicle to, specific points in the nervous system of all species. MALIGNIN, ASTROCYTIN, RECOGNIN M and RECOGNIN L are RECOGNINS.

Still another aspect of this invention is the production from biological fluids of two new products, TARGET-ATTACHING-GLOBULINS (TAG), which are so named because they are produced by two reactions, the first reacting biological fluids with a synthetic complex containing physiochemical configurations which mimic those of the MALIGNIN, RECOGNIN L and RECOGNIN M and called TARGET, the second, cleaving the specific TAG from the complex, and by the measure of the TAG so produced obtaining a quantitative indication from the biological fluids of living organisms whether there is present a tumor in that organism; hence a diagnostic test for tumors. Because TAG products and ANTI-MALIGNIN are physicochemically complimentary to MALIGNIN, they are termed CHEMORECIPROCALS.

It has been further discovered that two quantitatively and qualitatively distinct TAG products can be produced depending upon the time permitted for the reaction of serum with the specific TARGET reagent used, and depending upon the time permitted for the cleavage of the product which has been complexed.

After examining the amounts of these products which could be produced from a number of different individuals with brain tumors and various other medical disorders, as well as in those with no apparent disease process, it became apparent that the amounts of those two new products which could be produced in a given individual was indicative of whether that individual had a brain tumor, hence a novel serum diagnostic test for brain tumors has been discovered.

The utility of these new products, in addition to their use to diagnose from serum and other biological fluids the presence of brain and other tumors, is illustrated by the demonstration that TAG and anti-RECOGNIN compounds attach to glial tumor cells preferentially in histological section of brain tumor and surrounding tissue removed at surgery of the brain tumor. This preferential labelling by TAG and Anti-RECOGNINS of tumor cells is demonstrated through standard immunofluorescent techniques. Thus a new method is also available for determining through histological examination with a new degree of certainty whether tumor cells have penetrated to the very edges of the tissues removed indicating the likelihood that tumor still remains in the brain or other organ, or that tumor cells are absent from the periphery of the tissue removed, indicating the possibility that all of tumor has been removed from the brain or other organ. In addition, TAG and Anti-RECOGNINS produced as described have been found to be cytotoxic for glioma brain tumor cells grown in tissue culture in vitro. This high affinity for tumor cells in another medium, here grown in tissue culture, is further evidence of the specific-coupling potential of the new products TAG, and explains the adoption of the name TARGET-ATTACHING-GOBULINS (TAG) as do TAG's properties in regard to the synthetic product TARGET, and to tumor cells in histological section. Further, the cytotoxicity of TAG and anti-RECOGNINS for tumor cells provides an additional new diagnostic test for serum of patients who are suspected of suffering from a tumor. Thus, for example, the serum or other body fluid of these patients is reacted with TARGET to produce TAG and the product TAG is tested in tissue culture growths of tumor cells for cytoxicity. Both the concentration of TAG and the degree of cytoxocity manifested by the TAG which can be produced from a given individual's serum may be not only diagnostic but also of value in tracing the course of the disorder preoperatively and postoperatively in a given patient. Coupling of radioactive and dye tracers to TAG provides new TAG products which are useful in vivo in the diagnoses of tumors and in their exact localization. Thus the injection of suitably labelled TAG either intra-arterially or intravenously, into the cerebrospinal fluid, or directly into brain tissue or its cavities, permits the demonstration by radioactive means, or by visualization of the coupled dye, of the presence of a brain tumor, for it is only to the tumor cells that the TAG specifically attaches. Further, this method permits the precise visualization of the location of the brain tumor. This can be seen to be an improvement of this in vivo diagnostic method using anti-ASTROCYTIN produced in rabbit blood to label the brain tumor, because the use of TAG produced from human serum avoids the possibility of foreign protein reactions. Since TAG and anti-RECOGNIS have the chemical specificity which permits preferential attachement to ASTROCYTIN precursor containing tumor cells both in vitro and in vivo, these products may also be used therapeutically, as well as diagnostically, when coupled, e.g., with radioactive, proton capture agents, or other toxic physical or chemical agents, so that these toxic substances may be localized preferentially through these compounds' specificity of attachement in the tumor cells as compared to their neighboring normal cells. This selectivity is universally recognized as the crucial, or at least one crucial factor for achieving effective chemical or physical therapy of tumors, and a factor which has hitherto not been achieved. Thus TAG has demonstrated efficacy in attaching preferentially to the tumor cells, and should have promise as a new therapeutic product for these reasons.

In the serum of patients with malignant tumors, as will be seen in the examples below, one type of TAG, SLOW-TAG (S-TAG) as distinguished from FAST-TAG (F-TAG), can be produced in relatively greater amonts from a given volume of serum than in patients without such tumors. This suggests that either one of TAG'S naturally occuring precursors (P-TAG) is increased in concentration or that other factors exist which favor the relative in vitro production of S-TAG over F-TAG.

The possible relationship of the function of the actual synthetic products TARGET and TAG to their precursors, and in turn to the functions of postulated but not demonstrated cell "antigens" and circulating "antibodies" to them which may exist in vivo has yet to be elucidated. Thus for example, in antibody-like fashion, F-TAG and S-TAG produce single discrete lines of reaction with ASTROCYTI in Ouchterlony gel diffusion, and the injection of TARGET in rabbits induces an increase in the yield of TAG products from rabbit serum after reacting with TARGET. The finding that there may be a normal level of a precursor resembling antibody to a cell antigen which is hidden in the nondividing cell raises a question as to the possible function of the pair. It is here proposed that TAG precursor (P-TAG) and TARGET-like substances exist in vivo which function in the control of cell proliferation and cell death. Thus, for example, the exposure of a cell constituent which normally is not directly exposed to serum proteins may occur during cell division. The exposure of this cell constituent could result in that constituent becoming converted to a TARGET-like substance to which the attachment of a P-TAG-like molecule from serum may then occur, which would stimulate cell division or inhibit it. Alternatively, a nondividing cell which is injured or malfunctioning may expose a TARGET- like substance to which the attachement of P-TAG-like molecules may be reparative. However, under certain cell conditions the attachement of P-TAG-like molecules may induce the destruction of the cell (e.g., ANTI-GLIOMA-TAG synthetically produced as here described is markedly cytotoxic to glioma tumor cells growing in tissue culture). This could thus represent a mirror of a normal mechanism for the control of cell division, and for either the repair or the removal of individual cells in the body throughout the life of the organism. If the exposure of cell constituents is abnormally increased to that abnormally large amounts of cell TARGET-like substances are formed, as may occur in rapidly dividing cancer cells such as in brain gliomas, an increase in the concentration of one type of serum P-TAG relative to another may be induced.

Whatever the actual function of the precursors, the increase in the relative amount of predominately one type of TAG, SLOW-TAG (S-TAG) which can be produced in vitro by the methods here described from the serum of patients with malignant tumors is the basis of the serum diagnostic test described in the examples which follow.

EXAMPLE I

Production of Crude ASTROCYTIN-Precursor-Containing Fraction

Human brain glioma tumor tissue, removed at surgery, is dissected free as possible of surface blood vessels and normal brain tissue. For a typical amount of dissected tumor tissue of 11 grams, the tissue is weighed into six 1.5 g. and two 1.0 g. aliquots. Each aliquot is then treated as follows.

Each aliquot is homogenized in neutral buffer solution by sonification or other mechanical means. For example, each aliquot is homogenized in 100 cc per g. of tissue of 0.005M phosphate buffer solution, pH 7, in a Waring blender. Homogenization should be done in the cold to prevent denaturation of proteins. For example, the blender should be precooled in a cold room at 0°-5° C. and operated for about only three minutes.

The homogenate is then centrifuged for clarification, for example at 80,000 times gravity for 30 minutes in a refrigerated ultracentrifuge. The soluble supernatant is decanted and kept in the cold. The insoluble residue is rehomogenized with a further 100 cc of neural buffer and centrifuged as before, and the second soluble extract combined with the first. Best yields are obtained when this procedure of homogenization and centrifugation is repeated until less than 50 micrograms of protein per ml. of solution are obtained in the supernate. With most tissue this is accomplished by the fifth extraction.

The solutions thus obtained are combined and concentrated by perevaporation with subsequent dialysis, as by dialysis against 0.006M phosphate buffer in the cold to produce a volume of 15 ml. The volume of this solution is noted, an aliquot is taken for total protein analysis, and the remainder is fractionated to obtain the protein fraction having a pK range between 1 and 4. The preferred method of fractionation is chromatography as follows.

The solution is fractionated in the cold room (4° C.) on a DEAE cellulose (Cellex-D) column 2.5×11.0 cm., which has been equilibrated with 0.005M sodium phosphate buffer. Stepwise eluting solvent changes are made with the following solvents (solutions): Solution (1) 4.04 g. $NaH_2PO_4$ and 6.50 are dissolved in 15 liters of distilled $H_2O$ (0.005 molar, pH 7); Solution (2) 8.57 g. $NaH_2PO_4$, is dissolved in 2480 ml. of distilled $H_2O$; Solution (3) 17.1 g. of $NaH_2PO_4$ is dissolved in 2480 ml. of distilled $H_2O$; (0.05 molar, pH 4.7); Solution (4) 59.65 g. of $NaH_2PO_4$ is dissolved in 2470 ml. distilled $H_2O$ (0.175 molar); Solution (5) 101.6 g. of $NaH_2PO_4$ is dissolved in 2455 ml. distilled $H_2O$ (0.3 molar, pH 4.3); Solution (6) 340.1 g. of $NaH_2PO_4$ is dissolved in 2465 ml. of distilled $H_2O$ (1.0 molar, pH 4.1); Solution (7) 283.64 g. of 80% phosphoric acid ($H_3PO_4$) is made up in 2460 ml. of distilled $H_2O$ (1.0 molar, pH 1.0).

Add nervous tissue extract, 6 to 10 ml. volume. Let it pass into column. Then overlay with Solution (1) and attach a reservoir of 300 ml. of Solution (1) to drip by gravity onto the column. Three ml. aliquots of effluent are collected by means of an automatic fraction collector. The subsequent eluting solutions are exchanged stepwise at the following elution tube numbers. Solution (2): at tube 88, bring solution on column to top of resin, then overlay and attach reservoir of 50 ml. of Solution (2); Solution (3): at tube 98, bring solution on column to top of resin, then overlay and attach reservoir of 75 ml. of Solution (3); Solution (4): at tube 114, bring solution on column to top of resin, then overlay and attach reservoir of 150 ml. of Solution (4); Solution (5): åt tube 155, bring solution on column to top of resin, then overlay and attach reservoir of 125 ml. of Solution (5); Solution (6): at tube 187, bring solution on column to top of resin, then overlay and attach reservoir of 175 ml. of Solution (7); continue eluting until at tube 260, elution is complete. Use freshly prepared resin for every new volume of tissue extract. Each effluent tube is quantitatively analyzed for protein. The elutes in the tube numbers 212 to 230 are combined, and contain the crude products from which ASTROCYTIN will be produced.

While data has been published on this crude material, called fraction 10B in the past, [*Protein Metabolism of the Nervous System*, pp 555-69 (Pleum Press, 1970); Journal of Neurosurgery, Vol. 33, pp 281-286 (September, 1970)] the cleavage from fraction 10B of the specific product herein called ASTROCYTIN has now been accomplished. Crude fraction 10B can be prepared as a product in amounts between 0.1 and 10 mg. per gm. of original fresh nervous system tissue from which it was obtained. In addition to an ASTROCYTIN-precursor it contains varying amounts of covalently bound carbohydrate residues including a number of hexoses, namely glucose, galactose, mannose; hexosamines, including glucosamine, galactosamine and mannosamine; and occasionally other sugars, such as fructose, ribose and perhaps rhamnose. It also contains large molecular weight protein products, several lipids and nucleic acids.

EXAMPLE 2

Production of Purified ASTROCYTIN from Crude ASTROCYTIN-Precursor-Containing Fraction The ASTROCYTIN-Precursor-Containing fraction is further isolated from contaminants. In the preferred embodiments, the material from Example 1 is chromatographed on Sephadex G-50 resin with a typical column of 40 cm. long, 2.5 cm. diameter, and 196 ml. volume. The pressure used is 40 mm. Hg.,; the flow rate is 35 ml. per hour, and the buffer is 0.05 molar phosphate buffer solution, pH 7.2. The first (flow through) peak contains ASTROCYTIN-Precursor together with impurities, whereas subsequent peaks contain only impurities.

In the preferred embodiment, the products in the above first flow-through peak are then concentrated on Sephadex G-15, then passed onto a column of Cellex-D with the same solutions (1) through (7) as Example 1, and the same elution steps as performed in Example 1. The products ASTROCYTIN is present as a sharp peak in the same tubes (number 212-230) as before, thus maintaining its behaviour on Cellex-D chromatography without the presence of a large number of contaminants.

Low molecular weight contaminants may then be removed by techniques known to the art, such as millipore disc filtration. In the preferred method, the product ASTROCYTIN is freed of salt and other small molecular weight contaminants by filtration through Millipore Pellicon Disc No. 1000, 13 mm., which retains substances of molecular weights greater than 1000 and permits to pass through those of molecular weight less than 1000. The product ASTROCYTIN remains on the Pellicon Disc, and is recovered from it by washing with Solution (1) of Example 1.

ASTROCYTIN is then obtained by isolating the compound having a molecular weight of about 8000 from the above solution. A preferred method uses thin layer gel (TLG) chromatograph as follows:

The apparatus used is the commercially available one designed by Boehringer Mannheim GmbH; Pharmacia Fine Chemicals and CAMAG (Switzerland). The resin 2.5 g. of Sephadex G-200 superfine is prepared in 85 ml. of 0.5M. NaCl in 0.02M. $Na_2HPO_4KH_2PO_4$ Phosphate Buffer ph 6.8 (6.6-7.0). Allow to swell two or three days at room temperature with occasional gentle mixing. (Magnetic and other stirrers should not be used). The swollen gel is stabilized for three weeks at refrigerator temperature; however, bacterial and fungal growth may interfere with the swollen gel. If the gel is to be kept for longer periods of time, a small amount of a bacteriostatic agent should be added (sodium Azide 0.02%). 2.5 g. of dry gel are used to make two 20×20 cm. glass plates of 0.5 mm. thick. The plates are either allowed to dry at room temperature for 10 minutes and transferred to a moist chamber where they can be stored for about two weeks, or they are used immediately after appropriate pre-equilibration. (Usually during the night for a minimum of 12 hours). The main function of equilibration is to normalize the ratio between the stationary and mobile phase volumes. With the pre-equilibrated plates in a horizontal position, substances to be determined are applied with micropipettes as spots or as a streak at the start line. 10 ml. to 20 ml. of 0.2-2% of protein solution is placed on the edge of a microscopic cover slide (18 by 18 mm.) and held against the gel surface. In a few seconds the solution will soak into the gel. All samples are first prepared on the cover slides and then quickly applied. If not enough material is used, it is difficult to locate individual spots after separation. If too much material is applied no defined separation occurs. The samples are diluted with buffer for easier handling and the separation of samples is carried in a descending technique with the plate at an angle of 22°. The flow rate of about 1-2 cm/hour is most suitable. Marker substances (such as cytochrome C, hemoglobin, myoglobin or bromophenol blue labeled albumin) are applied at different positions across the plate and also to serve as reference proteins for calculation of relative distance (mobility) of unknowns. After application of samples, the plates are replaced in the apparatus and the paper wick pushed slightly downwards to ensure good contact with the gel layer. The paper wick must not drip. Excess moisture is wiped off. The liquid solvent in the reservoir is kept constant at 1 cm. from the upper end of the vessel. The runs are usually completed in 4 to 7 hours depending on the progress of separation. With colored substances separation follows directly. The separated spots of protein are easily made visible by transferring them to a paper sheet replica of TLG plate after the chromatographic separation has been completed, and by staining them on the prewashed methanol +$H_2O$+ acetic acid—90:5:5, for 48 hours. The paper sheet is 3 mm. filter paper. A sheet of paper 20×18 cm. is placed over the gel layer and pressed (rolled) just enough to ensure contact with the gel. Care is taken not to trap air under the paper (replica) and not to disturb the gel layer. The liquid phase is soaked off from the gel layer by the paper and removed after about one minute, immediately dried in an oven at 60° temperature for 15 minutes and stained in the normal way with any of the routine staining procedures. Staining is performed by spraying the replica-paper with 0.03% diazotized sulfanilic acid in 10% Sodium Carbonate (Pauley's Reagent). Staining can also be accomplished with a saturated solution of Amido Black in Methanol-Acetic Acid (90:10v/v is used); the staining time is 5-10 minutes. For destaining, rinse with two volumes of the 90:10 methanol and acetic acid solution mixed with one volume of $H_2O$. It is difficult to obtain low background staining without very extensive washing. The plates themselves may also be dried at about 60° C. (in an oven with air circulation) but only if the ASTROCYTIN is to be stained. For isolation purposes, the plate should only be air dried at room temperature. Over-heating can led to cracking, but this can usually be avoided with at 50°-60° C. temperature which dries a sephadex G-200 plate in 15-30 minutes. The dry plates are allowed to swell for 10 minutes in a mixture of methanol +$H_2O$+ acetic acid (75:20:5) and stained in a saturated Amido Black in the same solvent system for five hours and subsequently washed by bathing for two hours in the same solvent before they are dried. For molecular weight determinations the distance from the starting line to the middle of each zone is measured with an accuracy of 0.05 mm. either directly on the print (replica) or on the densitogram. The result is expressed by the $R_m$ value defined as the ratio of the migration distance of the tested protein ($d_p$) to that of cytochrome C or myoglobin ($d_m$) which is used as the reference protein: Relating migration distance of tested substance to standard is the formula ($-R_m=d_p/d_m$). A straight calibration line is obtained by plotting the logarithm of the molecular weight of the standards used against the $R_m$. From this line the molecular weight of the unknown protein can be obtained. For most exact results mix equal parts of the protein sample solution with standard, in this case, Cytochrome C, before applying to the plate. By the above TLG procedure the produce ASTROCYTIN in observed as a discrete spot at a distance of approximately $0.83\pm0.02$ with reference to the standard Cytochrome C, yielding an approximate molecular weight of 8000 for ASTROCYTIN. Several discrete products are separated in this procedure from ASTROCYTIN on the basis of slight differences in molecular weight. Thus, three products carried as contamination to this point with molecular weight of approximately 64,000, 148,000 and 230,000, and one occasionally of molecular weight 32,000, have been detected and removed by the TLG methods described above. The product ASTROCYTIN is aspirated with the gel in which it is contained, in dry form, dissolved in Solution (1) and freed of resin by centrifugation or other similar means.

The product ASTROCYTIN which has been produced at this stage is soluble in distilled water, soluble at neutral and acid pH, and insoluble at alkaline pH and has a spectrophotometric absorption peak wavelength of 280 mu. It is a polypeptide with molecular weight, as stated above, of approximately 8000. Its covalently linked amino acids are shown by hydrolysis with 6N HCl then quantitative automatic determination to have the following average composition of amino acids:

|  | Approximate Number of residues |
| --- | --- |
| Aspartic acid | 9 |
| Threonine | 5 |
| Serine | 6 |
| Glutamic acid | 13 |
| Proline | 4 |
| Glycine | 6 |
| Alanine | 9 |
| Valine | 4 |
| ½ Cysteine | 2 |
| Methionine | 1 |
| Isoleucine | 2 |
| Leucine | 8 |
| Tyrosine | 2 |
| Phenylalanine | 3 |
| Lysine | 8 |
| Histidine | 2 |
| Arginine | 4 |
| Approximate Total | 88 |

Cysteic acid, hydroxyproline, norleucine, ammonia, isodesmosine, desmosine, hydroxyysine, lysinonorleucine and gamma-aminobutyric acid are all absent in detectable amounts, but a trace of glucosamine may be present.

From 11 grams of the starting brain tumor tissue in EXAMPLE 1, approximately 3 mg. of purified ASTROCYTIN is produced by the above methods.

EXAMPLE 2A

PRODUCTION OF "REELER" RECOGNIN

Reeler disease is a genetic disorder in which animals fail to achieve stable coordinated motor activity, producing a reeling state, due to the failure of migration of certain nerve cells to a particular place in the brain, the cerebellum, at a particular developmental time. Particular glial cells have been shown, in electron microscopic studies, to provide the vertical pole-like axes along which the nerve cells migrate to their new positions in the normal state. The failure of nerve cells to climb these glial fibers, in Reeler disease is thought to be due to some disturbance in the nerve cells or the glia or both.

Following the methods of Examples 1 and 2, Recognin from mouse reeler brain was produced and compared with Recognin produced from normal mouse brain. The molecular weight of the Recognin produced from all areas of normal mouse brain was 8,000. The molecular weight of "Reeler" Recognin was 3,600 to 5,000. "Reeler" Recognin is abnormal, as shown by its much smaller molecular weight. Furthermore, the amount of Recognin which can be produced rom the cerebellum of reeler mouse brain is much reduced when compared to the normal. This is shown in Table I.

TABLE I

| Recognin Concentration in Mouse Brain, mg/g. | | |
| --- | --- | --- |
|  | Normal | Reeler |
| Cerebellum (16-day old mouse) | 2.50 | 0.71 |
| Cortex (16-day old mouse) | 0.60 | 0.96 |
| Cortex (4-day old mouse) | 0.29 | 0.53 |
| Brainstem (16-day old mouse) | 0.90 | 1.64 |
| Whole Brain (17-day old mouse) | 1.27 | 1.53 |
| Whole Brain (1-day old mouse) | 5.00 | 5.86 |

Table I shows that while there is a marked decrease in the concentration of Recognin in cerebellum of Reeler mouse, there are the same or greater amounts of Recognins in other areas of the brain. The Recognin may not move from the other areas of brain to the cerebellum, or the slight increase in other areas of Reeler brain may reflect some compensatory action.

This pathological Recognin in Reeler brain is correlated with the inability for migrating brain cells to make the contacts they must in order to achieve proper placement, confirming the role of RECOGNINS in recognition and learning in cells.

By analogy the ANTI-RECOGNINS to Recognin produced from mouse reeler brain may be produced and used in mice in a manner similar to the uses of ANTI-ASTROCYTIN and ANTI-MALIGNIN, as described herein.

EXAMPLE 3

Production of MALIGNIN-Precursor in Artifical Cancer Cell Culture Fermentations Generally, sterile technique is scrupulously maintained.

All solutions (e.g. Hank's Balanced Salt (BSS), F-10 Nutrient medium, fetal calf serum, trypsin solution) are incubated at about 35° C. in a water bath for approximately 20 minutes or more before use.

Cells are removed from tumor tissue and grown in vitro for many generations using a suitable medium, such as described below. Pre-rinse beakers to be used with a sterilizing solution, for example 12-proponal plus amphyl or creolin solution.

In the preferred embodiment, the artificial cancer cells (i.e., cells grown in vitro for many generations) are grown in 250 ml. flasks. The liquid medium in which the cells are growing is discharged into the pre-rinsed beakers. The cells are growing is discharged into the pre-rinsed beakers. The cells are then washed gently with 5–10 ml. of Hank's BSS or other similar solution for about 30 seconds. Avoid agitation. All walls and surfaces are washed. The solution is clarified of cells by centrifugation in the cold from minutes at 3,000 rpm. The medium is poured into a beaker as above. Add a small amount of buffered proteinase enzyme solution and rinse quickly to avoid digestion of the cells. In the preferred method, 1-2 ml. of trypsin solution (EDTA) is added and rinsed for only 10 seconds. Pour off the trypsin solution.

Add a similar volume of fresh trypsin solution and incubate until the cells are seen to be separated from the walls of the chamber through microscopic observation. This usually requires 5-10 minutes. Add a suitable growth medium, such as 50 ml. of a solution of 7-10 percent solution of fetal calf serum in 100 ml. of F-10 Nutrient medium.

Twenty five ml. of the fresh medium with cells is transferred to a new growth chamber for propagation. Both chambers are placed in an incubator at 35° C. for approximately seven days. By the procedure of this Example to this point, an artificial cancer cell culture is divided into two fresh cultures approximately every seven days. This entire procedure may be repeated as often as desired, at approximately seven-day intervals, for each growth chamber. Thus, the number of cells growing in vitro may be doubled approximately every seven days.

The cells may be extracted for the production of MALIGNIN after approximately seven days of growth. For example, cells growing in each 250 ml. growth chamber as described above, may be recovered as follows.

The medium is transferred to a centrifuge tube and centrifuged at 3,000 rpm in the cold for 10 minutes. The medium is discarded. The cells remaining in the growth chamber are scraped from the chamber walls and washed into the centrifuge tubes with neutral buffer solution. The cells are washed twice with neutral buffer solution, centrifuged again at 3,000 rpm in the cold, and the medium is discarded. The washed cells are suspended in 10 ml. of neutral phosphate buffer until ready for extraction of crude MALAGNIN-Precursor-Containing fraction.

EXAMPLE 4

Production of Crude MALIGNIN-Precursor-Containing Fraction

Washed cells suspended in neutral buffer from Example 3 are mechanically disrupted under conditions which avoid denaturation of most proteins. In the preferred method, the washed cells are treated in the cold with a sonifier for 20 seconds.

After sonification the cell residues are centrifused at 30,000 rpm for 30 minutes and the supernatant decanted. Ten ml. aliquots of buffer solution are used to wash remaining cell residues. Sonify and centrifuge as above and combine the supernatants. Repeat the process once more.

The combined supernant is perevaporated to reduce the approximate 30 ml. volume to about 6-7 ml. An aliquot is taken for total protein analysis and the remainder is fractionated according to the methods of EXAMPLE 1 for ASTROCYTI Precursor.

EXAMPLE 5

Production of Purified MALIGNIN Product from Crude MALIGNIN-containing Fraction

The product MALIGNIN is further isolated from contaminants by the methods of EXAMPLE 2 for ASTROCYTIN.

In the TLG step of the preferred embodiment, the product MALIGNIN is observed as a discrete spot at a distance of approximately $0.91 \pm 0.02$ with reference to the standard cytochrome C, yielding an approximate molecular weight of 10,000 for MALIGNIN.

The product MALIGNIN which has been produced at this stage is soluble in distilled water, soluble at neutral or acid pH, and insoluble at alkaline pH and having a spectrophotometric absorption peak of 280 mu. It is a polypeptide with molecular weight of approximately 10,000.

The molecular weights of MALIGNIN produced in fermentation cultures stabilized in successive generations of the cultures as shown by the thin layer gel chromatography determinations are set forth in Table II. The reproductivity of the molecular weight determinations is remarkable in view of the inherent limitations of TLG chromatography.

TABLE II

| Reproducability of Molecular weight of Malignin produced. | | | | | |
|---|---|---|---|---|---|
| Run No. | Mol. Wt. | Run No. | Mol. Wt. | Run No. | Mol. Wt. |
| 1 | 9,500 | 9 | 10,100 | 17 | 10,180 |
| 2 | 8,900 | 10 | 10,180 | 18 | 10,190 |
| 3 | 10,000 | 11 | 10,180 | 19 | 10,190 |
| 4 | 10,050 | 12 | 10,180 | 20 | 10,180 |
| 5 | 10,100 | 13 | 10,180 | 21 | 10,000 |
| 6 | 10,000 | 14 | 10,050 | 22 | 9,500 |
| 7 | 10,150 | 15 | 10,180 | 23 | 10,180 |
| 8 | 12,500 | 16 | 10,190 | | |

MALIGNIN'S covalently linked amino acids are shown by hydrolysis with 6N HCl then quantitative determination to have the following average composition of amino acids:

| | Approximate Number of Residues |
|---|---|
| Aspartic acid | 9 |
| Threonine | 5 |
| Serine | 5 |
| Glutamic acid | 13 |
| Proline | 4 |
| Glycine | 6 |
| Alanine | 9 |
| Valine | 6 |
| ½ Cysteine | 1 |
| Methionine | 2 |
| Isoleucine | 4 |
| Leucine | 8 |
| Tyrosine | 3 |
| Phenylalanine | 3 |
| Lysine | 6 |
| Histidine | 2 |
| Arginine | 5 |
| Approxiamate Total | 89 |

The amino acids cysteic acid, hydroxyproline, norleucine, ammonia, isodesmosine, desmosine, hydroxylysine, lysinonorleucine and gamma-aminobutyric acid being absent in detectable amounts.

A typical yield of pure MALIGNIN from twelve 250 ml. reaction chambers of EXAMPLE 3 together is approximately 1 mg. of MALIGNIN.

EXAMPLE 5A

Production of RECOGNIN L

Malignant cells grown in tissue culture, a lymphocytic lymphoma line of cells designated P₃ G, were obtained from Mason Research Institute, Rockville, Md.

Approximately 1 gm of packed cells of each of these were not further propagated upon receipt but extracted immediately according to the identical protocol used for producing Malignin from glioma cells (EXAMPLES 3, 4 and 5). Thus, the entire medium plus cells was transferred to centrifuge tubes with cold 0.005M phosphate buffer, pH 7, and centrifuged at 3,000 rpm in the cold for 10 minutes, the medium discarded, the cells washed twice with cold buffer, centrifuged again twice as before, and the washings discarded. The washed cells were suspended in the same buffer and disrupted by sonication for 20 seconds. The cell residues were centrifuged at 30,000 rpm for 30 minutes, the solubilized protein in the supernatant decanted and collected, and the cell residues sonified twice more, until no further appreciable protein was solubilized. The solubilized protein was concentrated and the recognin cloven and purified by Cellex D (BioRad) and Sephadex 200 (Pharmacia) gel chromatography. The yield, molecular weight, amino acid composition, behavior on thin layer gel chromatography and immunological properties of this polypeptide similar to those of Astrocytin and Maligin. The yield in the case of P₃G cells was approximately 1 mg/g wet weight of cells.

The covalently linked amino acids of Recognin L are shown, by hydrolysis (in vacuo) with 6N HCL at 108° C. for 12 hours followed by quantitative determination, to have the following average composition of amino acids (the nearest integer for the mole number of each amino acid is the average of two separate determinations):

|  | Number of Residues |
|---|---|
| Threonine | 5 |
| Serine | 5 |
| ½ Cysteine | 1 |
| Methionine | 1 |
| Valine | 6 |
| Isoleucine | 4 |
| Phenylalanine | 3 |
| Lysine | 6 |
| Histidine | 2 |
| Arginine | 5 |
| Aspartic Acid | 8 |
| Glutamic Acid | 10 |
| Leucine | 7 |
| Tryosine | 1 |
| Proline | 5 |
| Glycine | 13 |
| Alanine | 10 |
|  | 92 |

EXAMPLE 5B

Production of RECOGNIN M

Malignant cells grown in tissue culture, a mammary carcinoma cell line designated MCF-7, were obtained from Mason Research Institute, Rockville, Md.

Approximately 1 gm of packed cells of MCF-7 was not further propagated upon receipt but extracted immediately according to the protocol used for producing Malignin from glioma cells. (EXAMPLES 3, 4 and 5). Thus, the entire medium plus cells was transferred to centrifuge tubes with cold 0.005M phosphate buffer, pH 7, and centrifuged at 3,000 rpm in the cold for 10 minutes, the medium discarded, the cells washed twice with cold buffer, centrifuged again twice as before, and the washings discarded. The washed cells were suspended in the same buffer and disrupted by sonication for 20 seconds. The cell residues were centrifuged at 30,000 rpm for 30 minutes, the solubilized protein in the supernatant decanted and collected, and the cell residues sonified twice more, until no further appreciable protein was solubilized. The solubilized protein was concentrated and the recognin cloben and purified by Cellex D (BioRad) and Sephadex 200 (Pharmacia) gel chromatography. The yield, molecular weight, amino acid composition, behavior on thin layer gel chromatography and immunological properties of this polypeptide is similar to those of Astrocytin and Maligin, the previous two cancer recognins described. The yield in the case of MCF-7 cells was approximately 1 mg/g wet weight of cells.

The covalently linked amino acids of Recognin M are shown, by hydrolysis (in vacuo) with 6N HCL at 108° C. for 12 hours followed by quantitative automatic determination, to have the following average composition of amino acids (the nearest integer for the mole number of each amino acid is the average of two separate determinations):

|  | Number of Residues |
|---|---|
| Threonine | 5 |
| Serine | 5 |
| ½ Cysteine | 1 |
| Methionine | 1 |
| Valine | 6 |
| Isoleucine | 4 |
| Phenylalanine | 3 |
| Lysine | 6 |
| Histidine | 2 |
| Arginine | 5 |
| Aspartic Acid | 9 |
| Glutamic Acid | 11 |
| Leucine | 8 |
| Tryosine | 2 |
| Proline | 4 |
| Glycine | 9 |
| Alanine | 9 |
|  | 90 |

The unique structures of MALIGNIN, ASTROCYTIN, RECOGNIN M and RECOGNIN L were confirmed by an exhaustive computerized search which compared their compositions with virtually all known protein substances.

The amino acid composition of MALIGNIN and ASTROCYTIN, their absolute and relative amounts of each amino acid component in terms of the total number of amino acid residues per mole, and their absolute and relative amounts of each amino acid component in terms of the molecular weight of the molecule, were submitted to matrix computer analysis against the largest known library of protein structure in the world, that of the National Biomedical Research Foundation, Washington, D.C. No structure identical to or even very close to that of ASTROCYTI, MALIGNIN, RECOGNIN M or RECOGNIN L was found in the matrix analysis comparison with several hundred thousand proteins and protein fragments.

The only proteins that were structurally related in any way are shown in Table III with their individual amino compositions and molecular weights for comparison. The computer is programmed to identify, from the several hundred thousand possibilities, any degree of similarity in structure. Thus, for example, proteins of molecular weight much larger or smaller will not match, nor those with less than 85 or greater than 95 residues, nor those with less than 10 or greater than 15 glutamic acid residues, nor those with less than 6 or greater than 11 aspartic residues, and so on for each of the twenty amino acids involved.

the remaining several hundred thousand protein fragments in the computer memory bank.

Respiratory proteins may contain metals and/or heme components in their in situ state, but the isolated protein fragment, e.g., for apocytochrome $b_5$ contains neither. Additional microanalysis of Astrocytin and Malignin has shown them to be free of iron, sulfur, phosphorus and magnesium (all less than 0.01%), and the spectral characteristics show typical absorption at 280 mu. Upon recombination of heme with apoprotein,

TABLE III

COMPARISON OF THE STRUCTURES OF RECOGNINS TO NEAREST STRUCTURES BY COMPUTER SEARCH

|  | Astrocytin | Malignin | Recognin M | Recognin L | Cytochrome $b_5$ | Ferredoxin Luc. G1 | Ferredoxin Alf. | Acyl-Carrier E. Coli | Neurophysin Bovine | Neurophysin Pig | Gonadotropin Releas. |
|---|---|---|---|---|---|---|---|---|---|---|---|
| Aspartic acid | 9 | 9 | 9 | 8 | 9 | 10 | 8 | 7 | 2 | 3 | 0 |
| Threonine | 5 | 5 | 5 | 5 | 6 | 4 | 6 | 6 | 2 | 2 | 0 |
| Serine | 6 | 5 | 5 | 5 | 5 | 7 | 8 | 3 | 6 | 7 | 1 |
| Glutamic acid | 13 | 13 | 11 | 10 | 14 | 13 | 13 | 14 | 9 | 9 | 0 |
| Proline | 4 | 4 | 4 | 5 | 3 | 5 | 3 | 1 | 8 | 7 | 1 |
| Glycine | 6 | 6 | 9 | 13 | 6 | 7 | 7 | 4 | 16 | 14 | 2 |
| Alanine | 9 | 7 | 9 | 10 | 4 | 6 | 9 | 7 | 6 | 7 | 0 |
| Valine | 4 | 6 | 6 | 6 | 4 | 6 | 9 | 7 | 4 | 2 | 0 |
| ½ Cysteine | 2 | 1 | 1 | 1 | 0 | 5 | 5 | 0 | 14 | 14 | 0 |
| Methionine | 1 | 2 | 1 | 1 | 1 | 0 | 0 | 1 | 1 | 1 | 0 |
| Isoleucine | 2 | 4 | 4 | 4 | 4 | 4 | 4 | 7 | 2 | 2 | 0 |
| Leucine | 8 | 8 | 8 | 7 | 7 | 10 | 6 | 5 | 6 | 7 | 1 |
| Tyrosine | 2 | 3 | 2 | 1 | 3 | 3 | 4 | 1 | 1 | 1 | 1 |
| Phenylalanine | 3 | 3 | 3 | 3 | 3 | 3 | 2 | 2 | 3 | 3 | 0 |
| Lysine | 8 | 6 | 6 | 6 | 7 | 5 | 5 | 4 | 2 | 2 | 0 |
| Histidine | 2 | 2 | 2 | 2 | 7 | 1 | 2 | 1 | 0 | 0 | 1 |
| Arginine | 4 | 5 | 5 | 5 | 3 | 2 | 1 | 1 | 7 | 5 | 1 |
| Asparagine | 0 | 0 | 0 | 0 | 0 | 0 | 1 | 2 | 3 | 2 | 0 |
| Tryptophane | 0 | 0 | 0 | 0 | 1 | 1 | 1 | 0 | 0 | 0 | 1 |
| Glutamine | 0 | 0 | 0 | 0 | 0 | 4 | 3 | 4 | 5 | 4 | 0 |
| Total No. Residues | 88 | 89 | 90 | 92 | 87 | 96 | 97 | 77 | 97 | 92 | 10 |
| Molecular Weight | 8,000 | 10,000 | 8,000 | 8,000 | 10,035 | 10,493 | 8,509 | | | | |

This 'fingerprint' thus has some 22 individual variables to match. Some substances will match on one, on four or on five variables but none match on all 22. In fact, none match in better than 14 variables leaving differences in 8 variables.

Thus, the closest fit is cytochrome $b_5$ (human). As seen in Table III, the alanine, argine, asparagine, aspartic acid, cysteine, glutamine, histidine, methionine and tyrosine and tryptophane residue numbers all differ appreciably to markedly from the Recognins. Because cytochrome $b_5$ contains 7 histidines while Astrocytin, Malignin, Recognin L and Recognin M contain only 2, they could not possibly have the same chemical structure.

The most unusual thing about the composition of Astrocytin, Malignin, Recognin L and Recognin M is the high concentration of glutamic acid. One would expect to find only 5 or 6 residues in 89.

Other next-closest fits are the ferrodoxins of leucaene glauca and of alfalfa, respectively, but these also differ markedly in four and six amino acids, respectively, and appreciably in two others, and in having 96 and 97 residues, respectively. The next-closest fit is the acyl-carrier protein of E. Coli 26, but this also differs markedly in eleven amino acids from Malignin, Astrocytin, Recognin L and Recognin M and has only 77 residues.

Some other brain proteins (neurophysin, bovine and pig, and gonadotropin releasing hormone) are listed in Table III to illustrate how much worse the match is for the typical absorption spectra between 400 and 450 m are restored.

Despite the structural uniqueness of Astrocytin, Malignin, Recognin L and Recognin M from all other proteins and protein fragments, it is noteworthy and perhaps of great importance, that the closest structures are those of respiratory proteins. It is well known to the art that many important relationships can be drawn from both a developmental genetic point of view and from a functional point of view in the type of structure represented. If the Recognins are new protein products whose in situ structural equivalents represent respiratory functions, and these proteins relate as is now shown to malignancy, then an opening has been found to solve one of the great puzzles of cancer—that is, how are the energetics satisfied for these voracious, rapidly reproducing malignant cells?

Aside from the theoretical importance of this discover the data above on the increase in the percentage of Malignin in more malignant cells, and the data provided below indicating that Anti-Malignin now only attaches to Malignin-like chemical grouping of the cancer cell, but having so attached is cytotoxic to the cells, come together meaningfully. If the malignin-like in situ compounds in cancer cells are respiratory proteins, since the Anti-Malignin products of this invention attach preferentially to these in situ compounds, then if functional respiratory groups are involved in this attachment, it is easy to understand how this results in death of the cancer cells.

The therapeutic possibilities for the Anti-Malignins, and other similar chemoreciprocals, are greatly strengthened by this structural information on Malignin and Astrocytin, as well as on the demonstrated relationship of the amount of Malignin to the degree of malignancy.

The molecular weights of the four recognins described with particularity herein, i.e., Astrocytin, Malignin, Recognin M and Recognin L, calculated from their amino acid composition, are close to each other. Thin layer gel chromatography with Sephadex G200 (Pharmacia) gave a molecular weight for both Recognin L and Recognin M of approximately 8,000, the same as that obtained with Astrocytin. Since the calculated molecular weight of Astrocytin, based upon quantitative amino acid analysis, is 9,690, the lower apparent molecular weight of 8,000 obtained on this layer chrometrography may be, as in the case of MCF-7 and $P_3G$, a function of the slightly lower net acidic charge of these three polypeptides compared to that of Malignin. The molar composition of the constituent amino acids of the four recognins also are in close agreement with each other and different from all other known polypeptides by computer comparison. The fact that the only four polypeptides whose compositions are remotely related are phylogenetically ancient anaerobic oxidation-reduction enzymes has led to the suggestion that this may be an important clue to the basis of the anaerobic advantage of malignant cells recognized for many years but whose basis has not previously been defined. Whether the minor differences between the four cancer recognins represent significant structural differences is as yet unknown. The composition of twelve of the seventeen amino acids detected is seen to be identical for each of the three products from those cells which were grown in tissue culture. The principle differences between the composition of Recognin M and Recognin L when compared to that of Malignin, are a decrease in aspartic acid, glutamic acid, leucine and tyrosine, and an increase in proline, glycine and alanine.

Despite these chemical differences, the four recognins are, to the present, indistinguishable immunologically in each mode tested: (1) each reacts equally well on Ouchterlony double diffusion with anti-malign antibody; and (2) separate immobilized (bound to solid support) antigen preparations of each showed them approximately equal in their ability to bind antibody from human serum regardless of the type of cancer the patient had that is, immobilized Recognin M was observed to bind antibody from the serum of brain glioma patients as well as did immobilized Malignin.

EXAMPLE 5A

Demonstration of Increased Yield, Degree of Malignancy, and Proportion of Malignin, by Provision of Greater Volume and Surface Area During Fermentation Examples 3 through 5 were repeated using 1000 cc. flasks instead of 250 cc. flasks. All quantities of reagents were increased threefold.

The yield of the product MALIGNIN after 7 days growth of inoculum was increased almost twofold by increasing the space available for malignant cell growth from 250 cc. to 1000 cc. Table IV shows the yield of total protein in mg. and the MALIGNIN produced as a percentage of aid total protein for successive generations of fermentation cultures in each size flask. Using 250 cc. flasks, the mean total protein produced was 17.5 mg. Using 1000 cc. flasks, the mean total protein produced was 40.4 mg.

Surprisingly, as the amount of malignant cell growth (degree of malignancy) was increased per seven-day growth period by providing greater space and surface for cell growth, the amount of MALIGNIN produced, as a percentage of total protein which is MALIGNIN increased from a mean of 10.7 percent using 250 cc. flasks to a mean of 28.3 percent using 1000 cc. flasks for a constant growth period of seven days.

The relationship between the proportion of MALIGNIN produced, and the degree of malignancy (i.e., as a function of the amount of malignant cell growth in vitro in seven days, measured as total protein produced) is shown in FIG. 4.

TABLE IV
Improved Yields in Successive Generations of Fermentation Culture Production of Malignin

| Flask Size | Malignin, mg. | Total Protein, mg. | % Malignin |
|---|---|---|---|
| 250 cc. | .33 | 6.4 | 5.1 |
| " | .16 | 6.7 | 2.4 |
| " | .21 | 8.9 | 2.4 |
| " | 1.3 | 26.3 | 4.8 |
| " | 1.4 | 21.6 | 6.4 |
| " | 2.6 | 17.9 | 14.4 |
| " | 1.8 | 16.4 | 10.7 |
| " | 1.3 | 13.4 | 9.8 |
| " | 2.0 | 17.8 | 11.3 |
| " | 2.3 | 18.9 | 12.0 |
| " | 2.1 | 19.4 | 10.8 |
| " | 1.6 | 13.8 | 11.6 |
| " | 2.2 | 15.1 | 14.6 |
| " | 4.4 | 21.6 | 20.4 |
| " | 3.3 | 14.0 | 23.2 |
| " | 2.2 | 23.0 | 9.7 |
| " | 2.1 | 23.2 | 9.0 |
| " | 2.8 | 22.3 | 12.5 |
| " | 2.4 | 18.9 | 12.7 |
| " | 2.4 | 24.5 | 9.8 |
| | Mean | 17.5 mg. | 10.7% |
| 1000 cc. | 9.8 | 41.3 | 23.6 |
| " | 7.2 | 25.4 | 28.4 |
| " | 5.9 | 24.9 | 23.6 |
| " | 11.7 | 37.5 | 31.2 |
| " | 13.3 | 44.8 | 29.8 |
| " | 16.5 | 56.5 | 29.4 |
| " | 9.5 | 41.3 | 22.9 |
| " | 10.7 | 38.8 | 27.5 |
| " | 12.5 | 41.6 | 29.9 |
| " | 13.3 | 46.7 | 29.4 |
| " | 11.6 | 45.2 | 25.7 |
| | Mean | 40.4 mg. | 28.3% |

FIG. 4 shows that the increased flask size results in approximately trebled proportions of MALIGNIN product.

FIG. 4 also demonstrates a relationship between MALIGNIN and malignancy. The interrupted line represents an ideal linear relationship. This demonstrated relationship is clearly not trivial since the proportion of MALIGNIN present increases as the cells become more unrestrained (pathological) in their growth. The normal in situ Recognin function relates, as previously stated, to the contact inhibition of growth of cells. The more pathological the growth of the malignant cells, the less contact inhibition operates, and the more MALIGNIN becomes the predominant protein.

Example 5A demonstrates that growth of artificial cancer cell culture in large size growth containers unexpectedly results in increased proportion of MALIGNIN produced, that is, in an increase in the percentage of total protein produced which is MALIGNIN. As used in this application, a large size growth container means one in which the ratio of the container volume to the volume of total medium which cells utilized in accordance with the methods of Example 3 is greater than about 8:1, for example, 7:1 to 10:1. Example 5A illustrates a ratio of about 8:1.

EXAMPLE 6

Production of TARGET Reagents from RECOGNINS

ASTROCYTIN, prepared as in EXAMPLE 2 above, or MALIGNIN, prepared as an EXAMPLE 5 above, or Recognin M or Recognin L is complexed with a carrier to produce TARGET reagent.

In the preferred embodiment, which is applicable to any RECOGNIN, ASTROCYTIN, MALIGNIN, RECOGNIN L or RECOGNIN M, is dissolved in 0.15M $NaH_2PO_4$-citrate buffer, pH 4.0. A bromoacetyl-resin, for example, bromoacetylcellulose (BAC) having 1.0 to 1.5 milliequivalents Br per gram of cellulose, stored in the cold, is prepared in 0.15M $NaH_2PO_4$ buffer, pH 7.2. Convert the buffer to pH 4 by pouring off the pH 7.2 buffer solution and adding 0.15M $NaH_2PO_3$-citrate buffer, pH 4.0. The RECOGNIN solution and the BAC solution are stirred together (10:1 BAC to RECOGNIN ratio) for 30 hours at room temperature, then centrifuged.

It is preferred that all sites on the BAC which are available to bind to RECOGNIN be bound. This may be accomplished as follows. The supernatant from the immediately preceding step is lyophilized and the protein content determined to indicate the amount of RECOGNIN not yet complexed to BAC. The complexed BAC-RECOGNIN is resuspended in 0.1M bicarbonate buffer pH 8.9, stirred 24 hours at 4° to permit the formation of chemical bonds between the BAC and the RECOGNIN. After the 24 hours, the suspension is centrifuged and supernatant analyzed for protein. The complexed BACRECOGNIN is now resuspended in 0.05M aminoethanol-0.1M bicarbonate buffer pH 8.9 in order to block any unreacted bromine. The suspension is centrifuged, and the supernatant is kept but not analyzed because of the presence of aminoethanol. Removal of all unbound RECOGNIN is then accomplished by centrifugation and resuspension for three washings in 0.15M NaCl until no absorbance is measured on the spectrophotometer at 266 mu. The BAC-RECOGNIN complex is now stirred in 8M urea for 2 hours at 38° C., centrifuged, then washed (three times usually suffices) with 8M urea until no absorbance is shown in the washings at 266 mu. The complex is then stirred at 37° C. in 0.25M acetic acid for 2 hours to demonstrate its stability. Centrifuge and the read supernatant at 266 mu—no absorbance should be present. This chemically complexed BAC-RECOGNIN is therefore stable and can now be used as a reagent in the methods described below; in this stable reagent form it is referred to as a synthetically produced complex whose physical and chemical properties mimic the stable cellbound precursor of the RECOGNIN when it is in a potential reactive state with serum components. For storing, TARGET reagent is centrifuged and washed until neutralized with 0.15M $NaH_2PO_4$ buffer pH 7.2.

TARGET reagents may be prepared from bromoacetyl liganded carriers other than cellulose, such as bromoacetylated resins or even filter paper.

EXAMPLE 7

Production of antisera to Astrocytin, Malignin, and TARGET

Antisera to Astrocytin, Malignin, or TARGET reagents may be produced by inducing an antibody response in a mammal to them. The following procedure has been found to be satisfactory.

One mg. of RECOGNIN is injected into the toe pads of white male rabbits with standard Freund's adjuvant, and then the same injection is made intraperitoneally one week later, again intraperitoneally ten days and, if necessary, three weeks later. Specific antibodies may be detected in the blood serum of these rabbits as early as one week to ten days after the first injection. The same procedure is followed for TARGET antigen by injecting that amount of TARGET which contains 1 mg. of Astrocytin or Malignin as determined by Folin-Lowry determination of protein.

The specific antibody to Astrocytin is named AntiAstrocytin. The specific antibody to Malignin is named Anti-Malignin. Similarly, the specific antibody to TARGET reagent is named Anti-Target.

These antibodies show clearly on standard Ouchterlony gel diffusion tests for antigen-antibody reactions with specific single sharp reaction lines produced with their specific antigen.

The presence of specific antibodies in serum can also be tested by the standard quantitative precipitin test for antigen-antibody reactions. Good quantitative precipitin curves are obtained and the micrograms of specific antibody can be calculated therefrom.

Further evidence of the presence of specific antibodies in serum can be obtained by absorption of the specific antibody Anti-Astrocytin onto Bromoacetyl-cellulose-Astrocytin (BAC-Astrocytin) prepared above. The antiserum containing specific Anti-Astrocytin can be reacted with BAC-Astrocytin. When the serum is passed over BAC-Astrocytin only the specific antibodies to Astrocytin bind to their specific antigen Astrocytin. Since Astrocytin is covalently bound to Bromoacetyl-cellulose the specific antibody, Anti-Astrocytin, is now bound to BAC-Astrocytin to produce BAC-Astrocytin-Anti-Astrocytin (BACA-Anti-Astrocytin). This is proved by testing the remainder of the serum which is washed free from BAC-Astrocytin. On standard Ouchterlony diffusion no antibodies now remain in the serum which will react with Astrocytin. It is therefore concluded that all specific antibodies (Anti-Astrocytin) previously shown to be present in the serum, have been absorbed to BAC-Astrocytin. Furthermore, when Anti-Astrocytin is released from its binding to BAC-Astrocytin it is thereby isolated free of all contaminating antibodies. This release of Anti-Astrocytin may be accomplished by washing the BACA-Anti-Astrocytin coupled with 0.25M accetic acid (4° C., 2 hrs.) which has been shown above not to break the BAC-Astrocytin bond.

The antibodies to TARGET show clearly on standard Ouchterlony gel diffusion tests for antigen-antibody reactions with specific single reaction lines produced with TARGET which show a line of identity with the line of reaction to ANTI-ASTROCYTIN or ANTI-MALIGNIN antisera (i.e., that produced to the injection of ASTROCYTIN or MALIGNIN themselves). Some rabbits, it has been noted, have levels of ANTI-TARGET in their blood prior to being injected with TARGET. These ANTI-TARGET substances, when reacted specifically with TARGET reagent as to be described in tests of human sera, lead to the production of approximately equivalent amounts of the two types of TAG, S-TAG and F-TAG (see later EXAMPLES).

EXAMPLE 8

Detection of Malignant Tumors by Quantitative Production in vitro of TARGET-ATTACHING-GLOBULINS (TAG) from Biological Fluids TARGET reagent prepared in accordance with EXAMPLE 6 is washed to remove any unbound RECOGNIN which may be present due to deterioration. The following procedure is satisfactory. TARGET reagent is stirred for two hours at 37° C. with acetic acid, centrifuged, the supernatant decanted, and the optical density of the supernatant read at 266mu. If there is any absorbance, this wash is repeated until no further material is solubilized. The TARGET is then resuspended is phosphate buffered saline, pH 7.2. (Standard S-TAG and F-TAG purified from previous reactions of human serum by the procedure described below can be used if available, as reference standards to test the TARGET reagent, as can whole rabbit serum which has been determined to contain S-TAG and F-TAG by other TARGET preparations).

The Slow-Binding (S-TAG) determination is performed as follows: Frozen serum stored more than a few days should not be used. Serum is carefully prepared from freshly obtained whole blood or other body fluid by standard procedures in the art. The following procedure has been found to be satisfactory. Blood is allowed to clot by standing for 2 hours at room temperature in a glass test tube. The clots are separated from the walls with a glass stirring rod, and the blood allowed to stand at 4° C. for a minimum of 2 hours (or overnight). The clots are separated the serum by centrifuging at 20,000 rpm at 4° C. for 45 minutes. The serum is decanted into a centrifuge tube and centrifuged again at 2000 rpm at 4° C. for 45 minutes. The serum is decanted and a 1% Solution of Methiolate (1 g. in 95 ml. water and 5 ml. 0.2M bicarbonate buffer pH 10) is added to the extent of 1% of the volume and serum.

Serum samples, prepared by the above or other procedures, of 0,2 ml. each are added to each of 0.25 ml. aliquots of TARGET suspension reagent containing 100-200 micrograms of RECOGNIN per 0.25 ml. TARGET reagent, in duplicate determination. The suspension is mixed at 4° C. in a manner to avoid pellet formation. For example, a small rubber cap rapidly shaken may be used for 1-2 seconds and then, with the tubes slightly slanted, they may be shaken in a Thomas shaker for about 2 hours or more. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2-0.3 ml. of 0.15M. Saline, centrifuged and the supernatants discarded.

The protein which remains attached to the TARGET is cleaved therefrom and quantitatively determined. For example, 0.2 ml. of 0.25M acetic acid is needed, the suspension shaken for 1 to 2 hours in a 37° C. incubator. The tubes are centrifuged at 2000 rpm at 4° C. for 30 minutes. The supernatant is carefully decanted to avoid transferring particles and the optical density of the supernatant is read at 280 mu. The value of the optical density is divided by a factor of 1.46 for results in micrograms per ml. serum protein (S-TAG). Duplicate determinations should not vary more than 5%. Any other procedure effective for determining protein content may be used, such as Folin-Lowry determination, but standards must be specified to determine the range of control and tumor values of S-TAG minus F-TAG concentration.

The Fast-Binding (F-TAG) determination is performed as follows: Frozen serum stored more than a few days should not be used. Serum is carefully prepared from freshly obtained whole blood or other body fluid by standard procedures in the art. The procedure given above in this EXAMPLE for serum preparation is satisfactory.

Serum samples, prepared by the above or other procedures are allowed to stand at 4° C. for 10 minutes less than the total time the S-TAG serum determinations were allowed to be in contact with TARGET reagent above [e.g. 1 hour 50 minutes if a "two hour" S-TAG determination was made]. This procedure equilibrates the temperature histories of S-TAG and F-TAG determinations.

Add 0.2 ml. samples of the temperature equilibrated serum to each of 0.25 ml. aliquots of TARGET suspension reagent containing 100-200 micrograms of RECOGNIN per 0.25 ml. TARGET reagent, in duplicate determination. The suspension is then mixed at 40° C. for approximately 10 minutes in a manner to avoid pellet formation. For example, a small rubber cap rapidly shaken may be used for 1-2 seconds and then, with the tubes slightly slanted, they may be shaked in a Thomas shaker for approximately 10 minutes. The TARGET reagent and protein bound to it are separated from the serum. One of the procedures which has been found to be satisfactory is the following. The tubes are then centrifuged at 2000 rpm for 20 minutes at 4° C., the supernatant decanted, the pellet which is formed by centrifugation washed 3 times by remixing and shaking at room temperature with 0.2-0.3 ml. of 0.15M Saline, centrifuged and the supernatants discarded.

The protein which remains attached to the TARGET is cleaved therefrom and quantitatively determined. The procedure described above in this EXAMPLE for determining S-TAG concentration is satisfactory. Any other procedure effective for determining protein content may be used, such as Folin-Lowry determination, but standards must be specified to determine the range of control and tumor values of S-TAG minus F-TAG concentration.

The final results are expressed as TAG micrograms per ml. of Serum, and equal S-TAG minus F-TAG. TAG values in nonbrain-tumor patients and other controls currently range from zero (or a negative number) to 135 or 140 micrograms per ml. of serum. In any result over 100 ug/ml., a repeat determination is indicated. Some other tumors may yield high TAG values, especially if secondary (metastic) tumors are present in the brain. TAG values in brain tumor patients currently range from 136 to 500 or more micrograms per ml. of serum. In the first "blind" study of 50 blood samples conducted according to the procedures of this EXAMPLE utilizing TARGET reagent prepared from Astrocytin and bromoacetylcellulose, 11 of 11 brain tumors and 28 of 32 normals were correctly identified. One of the 4 supposed normals (i.e., non-brain tumor controls) turned out to have a cancer of the thyroid gland which had apparently been successfully treated some years before. The three remaining normals were individuals aged 60–70 who were in poor health, possibly having nondiagnosed cancer. Of the remaining 7 samples, three out of three cases of Hodgkin's Disease were correctly identified; one sample in the tumor range (136–500 ug. TAG/ml.) corresponded to a patient having a severe gliosis, and three samples in the non-tumor range (0–135 ug. TAG/ml.) corresponded to patients having respectively, and intercranial mass diagnosis uncertain but non-tumor, and osteosarcoma (non-brain tumor) and a melanotic sarcoma (non-brain tumor).

A subsequent study conducted according to the procedure of this example utilizing TARGET reagent prepared from Malignan and bromoacetylcellulose correctly differentiated three out of three malignant brain tumors and all normals.

A still further study conducted according to the procedure of this example extended the total number of human serum specimens tested from 50 to 114. Half of the serum specimens were tested with Malignin-derived TARGET reagent and half were tested with the corresponding Astrocytin-derived reagent. The results of this study is summarized in Table V.

EXAMPLE 9

Diagnosis of Tumor Cells by Immunofluorenscence

The compounds Anti-Astrocytin, Anti-Malignin, and S-TAG have been shown to attach preferentially to tumor cells. This specificity permits use of three compounds to diagnose tumor cells in histology sections by conjugating dyes or radioactive substances to Anti-Astrocytin, Anti-Malignin, or S-TAG. Standard labeling techniques may then be used. A procedure using S-TAG is as follows.

One procedure which has been found satisfactory is a modified St. Marie procedure. Human brain tumor specimens are frozen and 5 micron thick sections cut. They are stored in a moist container at minus 70° C. for 4 to 8 weeks before staining. The conjugate may be a standard antiserum such as goat anti-rabbit conjugate. The conjugate is labeled by techniques known in the art with fluorescent or other labeling substance. Fluorescein labeled goat anti-rabbit conjugate as commercially-available may be used. The fluorescent technique used was a standard one in which a 1:200 to 1:400 solution of TAG is incubated for about 30 minutes or more on the tumor section, followed by washes to remove unattached TAG. Three washes with phosphate buffered saline has been found satisfactory. Conjugate incubation with fluorescein-labeled conjugate followed by washes is then performed, followed by microscopic inspection. Normal cells and their processes fail to stain both in tumor sections and in control sections of normal non-tumor brain. Fluorescence is brightly present in tumor glial cells and their processes.

TABLE V

| Normals* | | | | Malignant Brain Tumors, Primary | Malignant Other Tumors, Brain Secondaries | Malignant Other Tumors. No Brain Secondaries | Uncertain Cerebral Diagnosis |
|---|---|---|---|---|---|---|---|
| Serum TAG ug/ml | Serum TAG ug/ml | Serum TAG ug/ml | Serum TAG ug/ml | Serum TAG ug/ml | Serum TAG ug/ml | Serum TAG ug/ml | Serum TAG ug/ml |
| 124 | 19 | 54 | 65 | 459 | 270 | 36[4] | 165[c] |
| 113 | 55 | 27 | 113 | 397 | 257 | 31[5] | 144[9] |
| 105 | 51 | 41 | 130 | 236 | 188 | 442[14] | 13[9] |
| 130 | 82 | 21 | 79 | 137 | 205 | 288[14] | 209[10] |
| 127 | 44 | 27 | 61 | 298 | 157[7] | | 75[10] |
| 38 | 127 | 21 | 123 | 397 | | | 184[11] |
| 100 | 31 | 0 | 14 | 241 | | | 27[11] |
| 125 | 0 | 14 | 20 | 241 | | | 110[12] |
| 30 | 125 | 62 | 41 | 217 | | | 192[15] |
| 250[1] | 118 | 38 | 34 | 147 | | | |
| 39 | 89 | 93 | 93 | 127 | | | |
| 363[1] | 99[6] | 21 | 48 | 185 | | | |
| 4 | 13[2] | 0 | 20 | 253 | | | |
| 31 | 270[3] | 120 | 82 | 253 | | | |
| 42 | 7 | 16 | 20 | 565 | | | |
| 34 | 58 | 20 | 55 | 277 | | | |
| 76 | 24 | 113 | 0 | 137 | | | |
| 48 | 62 | 72 | | 78[13] | | | |
| 85 | 89 | | | 138 | | | |
| | 89 | | | 650 | | | |
| | | | | 160 | | | |

*Includes normals, non-tumor medical and surgical disorders. 1-very ill; undiagnosed. 2-Extra brain intracranial mass, undiagnosed, 3-Marked gliosis, 4-Malignant melanoma, 5-Osteosar-coma, 6-Brain cyst fluid, 7-Adenocarcinoma of colon, 8-Gastrectomy, 9-Headaches, 10-Emphysema, 11-Polymyalgia, 12-Colon cancer, 13-Convulsions, 14-Cancer of prostrate, secondaries to bone, 15-Clinically "normal", 18-Months earlier, when this abnormal serum TAG obtained: Now developed sever headaches, loss of smell and taste.

EXAMPLE 10

Demonstration that Anti-Astrocytin, Anti-Malignin and S-TAG are Cytotoxic to Tumor Cells Growing in Tissue Culture Standard tests for determining cytotoxicity may be used. Generally, the number of cells in a fixed counting chamber, usually arranged to contain about 100 live cells, is counted. These cells are then treated with the agent being tested and the number of cells which are still alive is counted.

In a standard test of cytotoxicity of S-TAG Solution obtained in accordance with the methods of EXAMPLE 8 against cells in tissue culture derived from a patient with a glioblastoma Grade III-IV, well characterized as of glial origin, S-TAG produced death of all cells in the counting chamber even when in high dilution of 1:100 and 1:1000, representing as little as 0.2 and 0.02 ug. of S-TAG per ml. of solution. Similar results are obtained with high dilutions of AntiAstricytin and Anti-Malignin.

Both the specificity exhibited in EXAMPLE 9 and the cytotoxicity demonstrated in EXAMPLE 10 are highly relevant to the therapeutic possibilities of Anti-Astrocytin, Anti-Malignin and S-TAG for brain tumors in man. These therapeutic users are in addition to the practical diagnostic potential of both of these phenomena for tumor tissue removed at operation but requiring diagnosis by histology already demonstrated herein.

EXAMPLE 11

Hydrolytic Cleavage of RECOGNINS

A solution of RECOGNIN, in this case either Astrocytin or Malignin at pH between 1 and 2 is allowed to stand in the cold. After 7 to 14 days, TLG chromatography shows the product to have been reduced in molecular weight by approximately 200. When the solution is allowed to stand longer, further units of approximately 200 molecular weight are cleaved every 7 to 10 days. Thus with Astrocytin the molecular weight is reduced from 8,000, and with MALIGNIN the molecular weight is reduced from 10,000, in each case by units of approximately 200 sequentially.

The physiochemical specificities of Astocytin are retained by each product down to approximately 4,000 molecular weight. The physiochemical specificities of Malignin are retained by each product down to approximately 5,000 molecuar weight. This is shown by Ouchterlony gel diffusion tests against Anti-Astrocytin and Anti-Malignin, respectively.

This cleavage can also be accomplished exzymatically, as with tryspin and other proteindases, with similar results.

The molecular weights of these compounds prepared by hydrolytic cleavage of RECOGNINS may be approximately defined by the following formulae:

For products having the physiochemical specificities of Astrocytin; $400 + 200 x = Y$.

For products having the physiochemical specificities of Malignin; $5000 + 200 x = Y$ wherein Y is the molecular weight of the product and X is an integer from 0 to 19.

EXAMPLE 12

Production of Artificial Tissue or Organ with RECOGNINS

A rigid walled tube of plastic, metal, or other suitable rigid material is dipped in or impregnated with a highly concentrated, [i.e., 10 mg./ml.] viscous solution of RECOGNIN, in this case either Astrocytin or Malignin, until all surfaces are fully coated with the RECOGNIN. Alternately, RECOGNIN solution is passed through and around the tube under pressure until all surfaces are fully coated. The tube is then dried in air or in vacuo, or lyophilized. The process of coating is repeated several times in order to build up multiple molecular layers of RECOGNIN coating.

The tube is now ready to be placed in a cavity or in a tissue which contains Astrocytin or Malignin-like precursors in the neighboring tissue or fluid of a living mammal. This artificial tissue or organ may be used to minimize or eliminate reaction which foreign substances without RECOGNIN coating would incite.

Artificial tissues or organs of other geometries may similarly be produced.

EXAMPLE 13

Malignin is useful in a serum diagnostic test for the detection of a wide variety of tumors, including non-brain malignancies. The results of determinations on individual sera, and remarks related thereto, are reported in the following table.

TABLE 1

| | ANTI-MALIGNAN ANTIBODY DETERMINATION IN NON-BRAIN CANCERS WITH MALIGNAN-BASED TARGET REAGENT | | | | | | Antibody bound, as Protein Complexes in micrograms/ml Serum | | | |
|---|---|---|---|---|---|---|---|---|---|---|
| Non-Brain[a] Malignancies | Number of Serums Studied | Number Abnormally Elevated | Number Borderline | Number in Normal Range[c] | % Elevated | % Elevated + Borderline | S-TAG Mean | (±S.D.) | Net TAG Mean | (±S.D.) |
| Carcinoma of: | | | | | | | | | | |
| Lung | 6 | 5 | | 1 | 83.3 | 83.3 | | | | |
| Breast[g] | 10 | 10 | | | 100.0 | 100.0 | | | | |
| Colon[g] | 7 | 7 | | | 100.0 | 100.0 | | | | |
| Rectum[g] | 6 | 5 | | 1 | 83.3 | 83.3 | | | | |
| Prostate | 2 | 2 | | | 100.0 | 100.0 | | | | |
| Bladder | 1 | 1 | | | 100.0 | 100.0 | | | | |
| Ovary | 4 | 2 | 1 | 1 | 50.0 | 75.0 | | | | |
| Kidney | 1 | 1 | | | 100.0 | 100.0 | | | | |
| Thyroid | 1 | 1 | | | 100.0 | 100.0 | | | | |
| Undifferentiated | 2 | 2 | | | 100.0 | 100.0 | | | | |
| Lymphoma | 10 | 9 | | 1 | 90.0 | 90.0 | | | | |
| Hodgkins' Disease | 6 | 5 | 1 | | 83.3 | 100.0 | | | | |
| Multiple Myeloma | 6 | 6 | | | 100.0 | 100.0 | | | | |
| Acute Myelogenous Leukemia Chronic | 2 | 2 | | | 100.0 | 100.0 | | | | |

TABLE 1-continued

ANTI-MALIGNAN ANTIBODY DETERMINATION IN NON-BRAIN CANCERS WITH MALIGNAN-BASED TARGET REAGENT

| Non-Brain[a] Malignancies | Number of Serums Studied | Number Abnormally Elevated | Number Border-line | Number in Normal Range[c] | % Elevated | % Elevated + Borderline | Antibody bound, as Protein Complexes in micrograms/ml Serum | | | |
|---|---|---|---|---|---|---|---|---|---|---|
| | | | | | | | S-TAG Mean | (±S.D.) | Net TAG Mean | (±S.D.) |
| Myelogenous Leukemia[c] Chronic | 5 | 5 | | | 100.0 | 100.0 | | | | |
| Lymphocytic Leukemia[c] | 3 | 2 | 1 | | 66.6 | 100.0 | | | | |
| Osteogenic Sarcoma | 1 | | | 1 | 0 | 0 | | | | |
| Melanotic Sarcoma | 4 | 3 | | 1 | 75.0 | 75.0 | | | | |
| Total Non-Brain Malignancies | 77 | 68 | 3 | 6 | 88.3 | 92.2 | 482.5 | (±202.8) | 168.1 | (±145.9) |
| Brain Cancer[d,g] | 85 | 80 | 1 | 4 | 94.1 | 95.3 | 456.3 | (±146.9) | 183.4 | (±116.3) |
| Total Malignancies | 162 | 148 | 4 | 10 | 91.4 | 93.8 | | | | |
| Non-Malignant Medical and Surgical Disorders | 51 | 3 | —[e] | 48 | 5.9 | — | 259.8 | (±115.8) | 59.5 | (±66.0) |
| Normal | 77 | 3 | —[f] | 74 | 3.9 | — | 280.3 | (±79.5) | 60.2 | (±46.9) |

Total Number 290; % correct = 91.4; 94.5% including borderline values.

Legend:
S-TAG is the micrograms per ml. serum of antibody bound in 2 hours incubation; F-TAG is that bound in 10 minutes incubation; Net TAG = (S-TAG)-(F-TAG). Net TAG normal values 0 to 134 micrograms per ml. serum. Elevated values: Net TAG 135 micrograms per ml. serum or greater, or S-TAG greater than 400 micrograms per ml. even if high F-TAG value results in Net TAG less than 135 micrograms per ml. Borderline values 100 to 134 micrograms per ml. The values for S-TAG were significantly different for Gps. I and II as compared with Gps. III and IV at a level of p less than 0.000001 and for Net TAG at a level of p less than 0.000001. All of these determinations were performed blind. Only those cases in which the clinical source of the serum was known, the clinical-pathological diagnosis established, and the serum received in good condition frozen in dry ice not longer than 48 hours from the time it was drawn are included in the study; 270 specimens had to be excluded on these bases. [a]Seven of these determinations performed with Astrocytin-based TARGET reagent: 1 cancer of colon, 1 cancer of thyroid, 3 Hodgkins' Disease, 1 osteogenic sarcoma, 1 melanotic sarcoma. [b]polycythemia vera. [c]Terminal cases: 1 leukemia excluded, some additional may also by excluded. [d]Eleven of these determinations performed with Astrocytin-based TARGET reagent. [e]Six cases originally borderline, then normal when repeated; one sickle cell anemia in crisis with renal insufficiency, 1 case of obesity, 1 of gout. [f]Eleven cases originally borderline, then normal when repeated. [g]Two cases of breast cancer, 1 of rectum and 1 of brain demonstrated normal values of serum TAG and 2 colon cancer, borderline values, on serial determination during course of cancer

EXAMPLE 14

Detection of Non-Brain Malignant Cells With Fluorescent Signal From TAG

The uses of TAG products coupled with a signal emitter such as a dye or a radioactive label to detect cancer cells is described previously and herein. In this EXAMPLE 14, the detection of non-brain malignant cells is described.

As described in EXAMPLE 8 utilizing human serum; in the determination of TAG, after the anti-malignin antibody was bound to the immobilized antigen and non-bound serum proteins washed away, the antibody was cloven from the binding with 0.25M acetic acid at 37° C. for 2 hours and the TARGET reagent separated from it by centrifugation. The TAG antibody solution was quantitated by means of its absorption at 280 μ. The TAG solutions were stored at −20° C., then thawed and combined, brought to pH 7 by titration with 6N NaOH, dialyzed against phosphate buffered saline pH 7, filtered and concentrated on Millipore Pellicon 1000 membranes, centrifuged to clear insoluble protein and the immune globulin complexes concentrated and freed of immunologically non-active compounds by Cellex D and Blue Sepharose CL6B (Pharmacia) chromatography. This human anti-malignin antibody reacts with antihuman gamma globulin in Ouchterlony double diffusion. When TAG is used with fluorescein conjugated to anti-human gamma globulin in standard double layer Coons immunofluorescence it stains malignant glia, breast carcinoma, ovarian carcinoma, adenocarcinoma of colon, and other types of cancer cells in postoperative and biopsy tissue sections, as well as in human sputum, bronchial washings, pleural effusion fluid, gastric aspirate and bladder urine. The concentration of protein in TAG which yield clear fluorescence when controls are negative, is 1 to 10 μg per section.

The production of a "purified" TAG was undertaken by reacting the sera from patients with a variety of cancers with bromoacetylcellulose-MALIGNIN by methods earlier described (EXAMPLE 8). The antibody bound in this reaction was cleaved with 0.25M acetic acid, quantified by measurement at O.D. 280 using a conversion factor of 1.46 for gamma globulin, frozen and stored at −20° C. This antibody was found to contain immunoglobulin as determined by anti-human gamma-globulin antiserum specific for gamma chains (BioRad Laboratories, Inc.) and with anti-FAB and anti-Fc fragments (Miles Laboratories). It also reacts with rabbit anti-human albumin (BioRad Laboratories).

It was found that whereas 10 to 50 micrograms of protein TAG are required to produce specific immunofluorescent staining of cells which contain Malignin, only 1 to 10 micrograms of purified protein TAG are required for this specific staining in all sections, and in a few, less than one microgram has been found to suffice.

It was found that the most active preparation of purified TAG is that which is eluted with the highest ionic strength elution, i.e., from 0.15M to 1.5M. Any method of production which uses this fact is useful; three preferred methods are given below.

Method I—Fractionation of TAG by chromatography with DEAE cellulose (Cellex D, BioRad Laboratories) was first employed with step-wise elution with increasing ionic strength and decreasing pH, the same sequence of eluants as that given in Example I for the production of Crude Astrocytin-Precursor-Containing Fraction. Good separation was obtained of the bulk of the protein into three fractions, Peak I obtained with Solution 1 (see Example 1) and Peak II obtained with Solution 6 and Solution 7. Ouchterlony double diffusion F—0.05M TRIS, 1.5M NaCl (pH 7.2)

In the following Table are shown the recoveries from each fraction, a semi-quantitative determination in each of the gamma-globulin and albumin in each, as well as the activity of each fraction in the immunofluorescent staining of cancer cells. (The plus sign indicates reaction, zerp mp reaction and plus/minus reaction in some cases).

TABLE

| Fraction | I | II | III | IV | V | VI | VII | VIII |
|---|---|---|---|---|---|---|---|---|
| Recovered | | | | | | | | |
| ug | 2,877 | 1,140 | 2,351 | 2,942 | 1,808 | 2,230 | 2,125 | 7,477 |
| % | 12.5 | 5.0 | 10.2 | 12.8 | 7.9 | 9.7 | 9.3 | 32.6 |
| Immunodiffusion Against: | | | | | | | | |
| Anti-human IgG. specific for gamma chains | +++ | ++ | ++ | + | o | + | ++ | +++ |
| Anti-human aluminum | + | + | + | ++ | +++ | +++ | +++ | +++ |
| Anti-Fab | + | ++ | o | ++ | + | o | ++ | ++ |
| Anti-Fc | ++ | ++ | + | ++ | + | o | + | o |
| Immunofluorescence | ± | ± | ± | ± | ± | ± | ± | +++ | showed the TAG in Peak I still to contain appreciable protein with albumin mobility, and while Peak II contained most of the albumin, appreciable IgG could be detected. Rechromatography of Peak I gave a progressively pure IgG until, after the seventh chromatography, essentially no albumin (less than 3%) could be detected by Ouchterlony gel diffusion in which 5 to 10 micrograms of human albumin was detectable with rabbit anti-human albumin. The IgG so obtained was prone to denaturation and loss of immunological reactivity after a few days standing at 0°–5° C.

Method II—A second fractionation of TAG was made with chromatography on Sepharose CL-6B (Pharmacia, Inc.) starting with low molarity buffer (0.0005M phosphate) and proceeding in two steps of 0.15M and 1.5M to elute the balance of the protein. As with the Cellex D, one passage was found to be inadequate to separate, and recycling slowly improved the product. Once again, the most active fraction vis-a-vis anti-malignin antibody was in the 1.5M fraction.

Method III—Chromatography with Sepharose CL-6B next to the glass fritted disc and Cellex D layered above the Sepharose proved to be the most satisfactory method.

The graphical representation in FIG. 1 shows the fractions obtained on chromatography of TAG utilizing Method III. After the first eluate of 200 mls., 50 ml. or smaller sub-fractions were collected. The protein content of each eluate was determined by the optical density at 200 mu with a uniform factor of 1.46 based on gamma globulin used to convert to micrograms for calculating recoveries. The absolute amount of protein requires correction in those fractions in which there is appreciable albumin. The points at which the stepwise solvent changes were made are indicated by arrows. The subfractions are designated by Roman Numerals I through VIII.

The solvents corresponding to letters A–F at the arrows were as follows:
A—0.01M TRIS (pH 7.2)
B—0.05M TRIS with 0.1M NaCl (pH 7.2)
C—PBS, 0.11M NaCl (pH 7.2)
D—PBS, 0.165M NaCl (pH 7.2)
E—PBS, 0.33M NaCl (pH 7.2)

FIG. 2 is a photograph showing the line of reaction between anti-human gamma globulin specific for gamma chains for each of Fractions I and II from above (left and below in photograph).

FIGS. 3a and 3b are photographs showing the use of TAG (Fraction VIII from above) to stain non-brain malignant cells. FIG. 3a is a stain of bronchogenic carcinoma cells in the bronchial washings of a patient; FIG. 3b is a stain of lymphoma cells in the pleural fluid of a patient. Non-cancer cells do not fluoresce. The TAG (1 to 10 ug in 0.1 ml phosphate buffered saline (PBS)) is applied to the surface of packed cells on a glass slide incubated 30 minutes, washed three times with PBS and then layered with fluoroscein-conjugated anti-human IgG diluted until non-malignant control tissues give essentially no fluorescence. The cells are visualized with a Zeiss fluorescent microscope using a tungsten lamp and filters BG 23, BG 12 and 500.

EXAMPLE 9B

Detection of Cancer Cells With Radioisotope Signal From Tag

In this Example, the feasibility of attaching a radioactive label to TAG is demonstrated. Second, the injection into animals of this radio-labeled TAG has been accomplished and shown to be safe and effective. Third, the radio-labeled TAG localized preferentially in the cancer tissue when compared to normal tissue, thus indicating that the specificity previously demonstrated in vitro of the preference for cancer cells which is conveyed by the use of specific anti-Malignin TAG products is confirmed in vivo.

The Labeling of TAG with 99m Technetium ($^{99m}Tc$)

Procedure for Labeling

1. Two preparations of TAG were used, here designated TAG-1 and TAG-2. TAG-1 and TAG-2 (concentration of each 0.4 mg/0.5 ml) were added to separate sterile evacuated vials.
2. To each vial was added 0.1 ml of a stannous chloride solution (10 mg $SnCl_2 \cdot 2 H_2O$ in 100 ml of 0.01N HCl). The vials were mixed for 3–4 minutes.
3. 0.1 ml. (6mCi) of $^{99m}Tc$-pertechne2tate (sodium salt) was added and mixed 2–3 minutes.

Procedure for determining labeling efficiency

Samples of the $^{99m}$Tc-TAG-1 and $^{99m}$Tc-TAG-2 were tested for labeling efficiency by descending paper chromatography using Watman No. 1 paper with 85% methanol as the solvent. A similar study was done with Sodium Pertechnetate-$^{99m}$Tc which acted as a control. After 2 hours, the papers were removed from the chromatography tank and divided in two sections: (1) 1 cm about the origin; (2) the remaining paper up to the solvent front. Each section was then counted in a gamma well scintillation counter and its content of radioactivity determined (cpm).

Approximately 50 lambda were plated on each paper strip.

Procedure for Antigen-Antibody Reaction

A portion of the labeled solution was also plated on an Ouchterlony gel plate to determine its ability to react with malignin in the antigen-antibody reaction. After a 3 hour period, the resulting sharp reactive lines were removed from the gel and their content of radioactivity measured. An equal portion of the gel not involved in the reaction was also removed and its content of radio activity was also measured as background.

Results

Labeling Efficiency

TABLE 1

| Labeling Efficiency of $^{99m}$Tc—TAG—1 and $^{99m}$Tc—TAG—2 | | | | |
|---|---|---|---|---|
| COMPOUND | SITE ON PAPER | CPM | % | CHEMICAL SPECIES |
| NaTcO$_4$—99 mTc | origin | 4.94 × 10$^5$ | 7.33% | reduced TcO$_4$— |
| NaTcO$_4$—99 mTc | solvent front | 6.25 × 10$^6$ | 92.67% | TcO$^4$— |
| TAG—1 | origin | 4.35 × 10$^6$ | 98.47% | TAG—99 mTc |
| TAG—1 | solvent front | 6.76 × 10$^4$ | 1.53% | TcO$_4$— |
| TAG—2 | origin | 1.96 × 10$^6$ | 98.01% | TAG—99 mTc |
| TAG—2 | solvent front | 3.98 × 10$^4$ | 1.99% | TcO$_4$— |

TABLE 2

| ANTIGEN-ANTIBODY RESECTION | | |
|---|---|---|
| GEL AREA | COUNTS PER MIN | % |
| TAG—2 line | 1.99 × 10$^6$ | 92.04% |
| Background gel | 1.72 × 10$^5$ | 7.96% |

Conclusions

The following conclusions were reached relative to the quality control tests employed:

1. $^{99m}$Tc-pertechnetate was reduced by stannous chloride to a more reactive oxidation state (+4+5).

2. The reduced pertechnetate labeled both the TAG-1 and TAG-2 preparations.

3. The $^{99m}$Tc-TAG-2 was tested for its ability to retain its activity and was found to retain its ability to react immunologically.

The Use of Radio Labeled TAG in vivo to Detect Cancer Cells

Wistar rats were injected intracerebrally with Cisgliome tumor cells which had had previous passages in rats and in tissue culture. The rats were observed for the first signs of growing tumor, such as weakness, tremor or unsteadiness. These symptoms first appear seven to 10 days from injection, and with fast growing tumors result in death within three to four days in many animals, and one week in all. As soon as symptoms appeared, the animals were injected with labeled TAG intravenously in the tail vein, then the animal anesthetized at varying times, the brain removed, the tumor dissected free of normal brain, and the radioactivity in each dissected specimen compared.

| Preliminary $^{99m}$Tc—TAG experiment | | | |
|---|---|---|---|
| | | Counts/gm/min. | |
| Animal | Sacrifice (hr. post injection) | Tumor wt., mg. | Tumor | Normal Brain |
| A | 1.25 | 1.9 | 149,100 | 13,400 |
| B | 5.30 | 6.0 | 16,200 | 6,600 |
| C | 7.21 | 23.0 | 53,000 | 5,300 |
| D | 24.10 | 29.0 | 66,700 | 7,500 |

Tumor and normal brain specimens were counted overnight in the gamma-well counter. All samples and standards were decay corrected for convenience to the mid-count of the first sample in the sequence.

Conclusion

The preferential localization of radioactivity in tumor as compared to normal tissue is demonstrated above.

I claim:

1. A method for diagnosing malignant tumors which comprises:
   (a) dividing a sample of body fluid into a first and second aliquot;
   (b) contacting said first aliquot with a complex of Malignin and an inert carrier for about two hours to allow protein to bind to said complex;
   (c) separating from said first aliquot said complex and the protein bound to it;
   (d) cleaving the bound protein from said complex;
   (e) quantitatively determining the amount of protein cleaved from said complex;
   (f) contacting said second aliquot with a complex of Malignin and an inert carrier for about 10 minutes to allow protein to bind to said complex;
   (g) separating from said second aliquot said complex and the protein bound to it;
   (h) cleaving the bound protein from said complex;
   (i) quantitatively determining the amount of protein cleaved from said complex;
   (j) comparing the amount of protein determined in step e, above, with that determined in step i, above; and correlating the difference between the two amounts with a predetermined standard value indicative of the tumor, wherein said Malignin is a product, derived from brain tumor cells, which forms a single line precipitate with its specific antibody in quantitative precipitin tests and in Ouchterlony gel diffusion tests, is soluble in water and aqueous solutions having an acid or neutral pH, and insoluble at an alkaline pH, has a spectrophotometric absorption peak wave length of 280 mu, a molecular weight of about 10,000 and an amino acid composition approximately as follows:

|  | Approximate No. of Residues |
|---|---|
| Aspartic Acid | 9 |
| Threonine | 5 |
| Serine | 5 |
| Glutamic Acid | 13 |
| Proline | 4 |
| Glycine | 6 |
| Alanine | 7 |
| Valine | 6 |
| ½ Cystine | 1 |
| Methionine | 2 |
| Isoleucine | 4 |
| Leucine | 8 |
| Tryosine | 3 |
| Phenylalanine | 3 |
| Lysine | 6 |
| Histidine | 2 |
| Arginine | 5 |
| Approximate Total | 89 | ammonia and the amino acids cysteic, hydroxyproline, norleucine, isodesmosine, hydroxylysine, lysinonorleucine and gammaaminobutyric acid being absent in detectable amounts.

2. The method according to claim 1 wherein said inert carrier complexed with Malignin is bromoacetylcellulose.

3. The procedure according to claim 1 wherein the body fluid is blood serum.

4. The procedure according to claim 1 wherein the bound protein is cleaved from said complex by contacting the protein-bound complex with aqueous acetic acid.

5. The procedure according to claim 1 wherein the cleaved protein is determined by a procedure comprising reacting the protein-bound complex with aqueous acetic acid, centrifuging the mixture and determining the optical density of the supernatant at about 280 m$\mu$.

6. The procedure of claim 2 wherein the complex of Malignin and bromoacetylcellulose is suspended in phosphate buffered saline at pH 7.2 prior to being contacted with the aliquots of body fluid.

7. The procedure of claim 6 wherein about 0.25 ml of said Malignin-bromoacetylcellulose suspension comprises about 100–200 micrograms of Malignin.

8. The procedure of claim 1 wherein the body fluid and the Malignin-carrier complex are contacted at about 4° C.

* * * * *